(12) United States Patent
Landesman

(10) Patent No.: US 9,901,297 B2
(45) Date of Patent: Feb. 27, 2018

(54) METHOD AND APPARATUS FOR TISSUE DISEASE DIAGNOSIS

(71) Applicant: BIOP MEDICAL, LTD., Netanya (IL)

(72) Inventor: Ilan Landesman, Ramat Gan (IL)

(73) Assignee: BIOP MEDICAL LTD. (IL)

( * ) Notice: Subject to any disclaimer, the term of this patent is extended or adjusted under 35 U.S.C. 154(b) by 623 days.

(21) Appl. No.: 14/376,427

(22) PCT Filed: Feb. 7, 2013

(86) PCT No.: PCT/IL2013/050117
§ 371 (c)(1),
(2) Date: Aug. 3, 2014

(87) PCT Pub. No.: WO2013/118124
PCT Pub. Date: Aug. 15, 2013

(65) Prior Publication Data
US 2015/0032008 A1    Jan. 29, 2015

Related U.S. Application Data

(60) Provisional application No. 61/596,262, filed on Feb. 8, 2012.

(51) Int. Cl.
*A61B 5/00* (2006.01)
*A61B 1/00* (2006.01)
(Continued)

(52) U.S. Cl.
CPC ........ *A61B 5/4331* (2013.01); *A61B 1/00009* (2013.01); *A61B 1/0638* (2013.01);
(Continued)

(58) Field of Classification Search
CPC ... A61B 5/4331; A61B 5/0062; A61B 5/0084; A61B 1/00009; A61B 1/0638; A61B 1/303
See application file for complete search history.

(56) References Cited

U.S. PATENT DOCUMENTS

| 5,421,339 A | 6/1995 | Ramanujam et al. |
| 5,623,932 A | 4/1997 | Ramanujam et al. |

(Continued)

FOREIGN PATENT DOCUMENTS

| WO | 98/24369 A1 | 6/1998 |
| WO | 2009/051728 A1 | 4/2009 |
| WO | 2011/066149 A1 | 6/2011 |

OTHER PUBLICATIONS

International Search Report for PCT application PCT/IL2013/050117, Issued by the EPO, dated Jul. 1, 2013.
(Continued)

*Primary Examiner* — Joseph Dietrich
(74) *Attorney, Agent, or Firm* — Akerman LLP

(57) ABSTRACT

A tissue diagnosis apparatus constituted of: a broad band light source arranged to irradiate a target area with broad band light; a narrow band light source arranged to irradiate the target area with narrow band light; at least one light sensor arranged to: sense the broad and narrow band light after interaction with the target area; a color sensor arranged to sense the broad band light after interaction with the target area; and a housing, the broad band light source, narrow band light source, light sensor and color sensor situated within the housing, wherein a control circuitry is arranged to: determine the image abnormality of the sensed broad band light, the spatial scattering of the sensed narrow band light and the chromatic impact of the interaction of the broad band light with the target area; and output a signal responsive to the identified image abnormality, spatial scattering and chromatic impact.

30 Claims, 20 Drawing Sheets

(51) Int. Cl.
   *A61B 1/06*   (2006.01)
   *A61B 1/303*  (2006.01)
(52) U.S. Cl.
   CPC ............ *A61B 1/303* (2013.01); *A61B 5/0062* (2013.01); *A61B 5/0084* (2013.01)

(56) References Cited

U.S. PATENT DOCUMENTS

| | | |
|---|---|---|
| 7,428,048 B1 | 9/2008 | Farkas et al. |
| 7,664,300 B2 | 2/2010 | Lange et al. |
| 7,706,862 B2 | 4/2010 | Alfano et al. |
| 2003/0013973 A1 | 1/2003 | Georgakoudi et al. |
| 2003/0231309 A1 | 12/2003 | Fulghum, Jr. et al. |
| 2007/0100207 A1 | 5/2007 | Ueno et al. |
| 2008/0194969 A1 | 8/2008 | Werahera et al. |
| 2009/0062662 A1 | 3/2009 | Zuluaga |
| 2010/0149315 A1 | 6/2010 | Qu et al. |
| 2010/0158330 A1 | 6/2010 | Guissin et al. |
| 2010/0210951 A1 | 8/2010 | Rahman et al. |

OTHER PUBLICATIONS

Written Opinion of the International Searching Agency for PCT application PCT/IL2013/050117, Issued by the EPO, dated Jul. 1, 2013.
Office Action for Parallel Chinese Application 201380017969.3, dated Dec. 12, 2015.

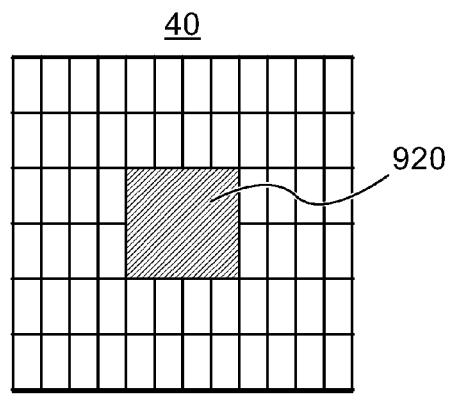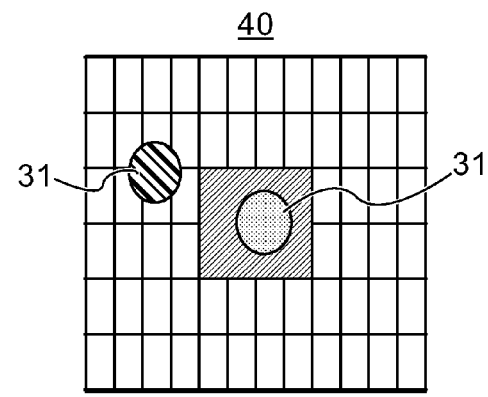
Fig. 20A    Fig. 20B
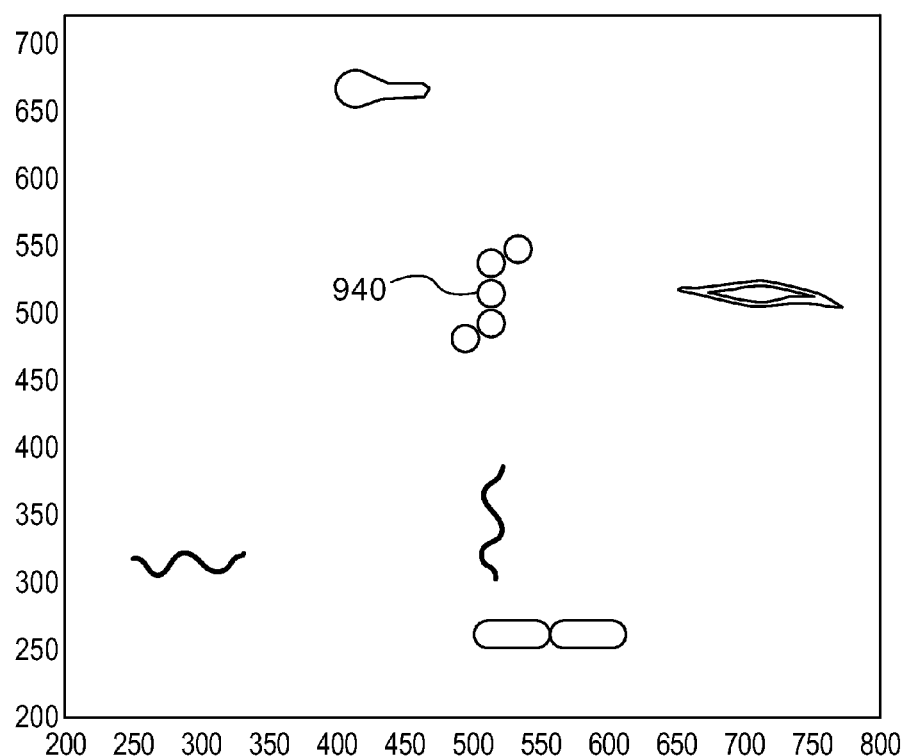
Fig. 21A

METHOD AND APPARATUS FOR TISSUE DISEASE DIAGNOSIS

CROSS-REFERENCE TO RELATED APPLICATIONS

This application claims priority from U.S. Provisional Patent Application Ser. No. 61/596,262, filed Feb. 8, 2012 and entitled "DIAGNOSTIC SYSTEM FOR DETECTION OF ABNORMAL CONDITION OF CERVICAL TISSUE", the entire contents of each of which are incorporated herein by reference.

FIELD OF THE INVENTION

The invention relates generally to the field of tissue abnormality diagnosis and in particular to a method and apparatus for optical diagnosis of tissue diseases.

BACKGROUND OF THE INVENTION

Cervical cancer is one of the common neoplasms of the female genital tract. Cervical cancer is the second malignancy in women worldwide and is one of the leading causes of women death in the third world. Early diagnosis of abnormal cells in the cervix prevents deterioration into fully cervical cancer and thus reduces morbidity and mortality. The pre-cancerous state is called Squamous Intraepithelial Lesion (SIL), and has two grades: low grade SIL and high grade SIL.

The uterine cervix is very good for screening purposes for several reasons. First, the tumoral changes occur in a specific area, called the transitional zone, around the "external of" (opening of the cervical canal into the vagina). Second, these are slow growing tumors. Third, this area is external in the body and can be easily analyzed by a Gynecologist.

The current screening method, called a Pap smear, has been used for decades. During a Pap smear, a large number of cells, obtained by scraping the cervical epithelium, are smeared onto a slide, or into a liquids tube, which is then fixed and stained for cytologic examination. Unfortunately, the Pap smear is unable to achieve a concurrently high sensitivity and high specificity due to both sampling and analysis errors. Estimates of the sensitivity and specificity of Pap smear screening range from 11-99% and 14-97%, respectively. As used herein, the term sensitivity is defined as the correct classification percentage on pre-cancerous tissue samples, and the term specificity is defined as the correct classification percentage of normal tissue samples. According to the National Cancer Institute (NCI), about 55 million Pap tests are performed each year in the USA. Of these, approximately 3.5 million are abnormal and require medical follow-up. Most of the abnormal tests are in fact falsely indicative of SIL.

Additionally, analyzing Pap smears is extremely labor intensive and requires highly trained professionals. A patient with an abnormal Pap smear indicating the presence of SIL needs to then undergo a diagnostic procedure called colposcopy, which involves colposcopic examination, and if needed biopsy and histology confirmation of the clinical diagnosis. Extensive training is necessary in order for a practitioner to perform colposcopy and its diagnosis accuracy is variable and limited, even in expert hands. Moreover, diagnosis is not immediate.

Thus, it would be desirable to provide a method for early detection of cervical cancer with improved specificity and sensitivity, which reduces the required skill level of the practitioner interpreting the results and shortens the diagnosis period.

One "in vivo" method of detection is Electrical Impedance Spectroscopy (EIS), which indicates the condition of the tissue by the change of impedance with frequency. Disadvantageously, EIS has positive predictive value (PPV) of only 72% and is an expensive process.

Thus, it would be desirable to provide a method and apparatus for detection of cervical pre-cancer that provides greater sensitivity and selectivity than prior art techniques. Additionally, it would be desirable to provide such a technique which is also cost effective.

SUMMARY

Accordingly, it is a principal object of the present invention to overcome at least some of the disadvantages of the prior art. In certain embodiments this is provided by A tissue disease diagnosis apparatus, the apparatus comprising: a control circuitry; a broad band light source arranged to output a broad band light and irradiate a target area of an organ with the output broad band light; a narrow band light source arranged to output a narrow band light and irradiate the target area of the organ with the output narrow band light; at least one light sensor in communication with the control circuitry, the at least one light sensor arranged to: sense the broad band light after interaction with the target area and output an image of the target area responsive to the sensed broad band light, and sense the narrow band light after interaction with the target area and outputs a signal responsive to the sensed narrow band light; a color sensor in communication with the control circuitry and arranged to sense the broad band light after interaction with the target area and outputs a signal responsive to the sensed broad band light; and a housing, the broad band light source, narrow band light source, at least one light sensor and color sensor situated within the housing, wherein the control circuitry is arranged to: identify an abnormality in the image output by the at least one light sensor, the abnormality identification responsive to one of the intensity and color of the image; determine the spatial scattering of the sensed narrow band light responsive to the output signal of the at least one light sensor; determine the chromatic impact of the interaction of the output broadband light with the target area, responsive to the output signal of the color sensor; and output a tissue information signal responsive to the image abnormality identification, the determined spatial scattering and the determined chromatic impact.

In one embodiment, the control circuitry is further arranged to determine the amount of absorption of the output narrow band light within the target area responsive to the signal output by the at least one light sensor responsive to the narrow band light, and wherein the output tissue information signal is further responsive to the determined absorption amount. In another embodiment, the at least one light sensor comprises: an imager arranged to output the image of the target area to the control circuitry; and a light sensor array arranged to output the signal responsive to the sensed narrow band light.

In one embodiment, the output narrow band light is coherent. In another embodiment, in the event that the determined spatial scattering of the sensed narrow band light is indicative of unhealthy tissue within the target area the control circuitry is further arranged to determine the amount of absorption of the output narrow band light within the target area responsive to the narrow band light sensed by the at least one light sensor, and wherein the output tissue information signal is further responsive to the determined absorption amount.

In one further embodiment, in the event that the determined absorption amount is not indicative of unhealthy tissue within the target area, the control circuitry is further arranged to: repeat the image abnormality identification; and repeat the determination of spatial scattering, wherein the output tissue information signal is further responsive to the repeated image abnormality identification and the repeated determined spatial scattering. In another further embodiment, in the event that the determined absorption amount is indicative of unhealthy tissue within the target area, the output tissue information signal comprises an indication that cervical intraepithelial neoplasia (CIN) is present within tissue of the target area.

In one further embodiment, in the event that the image abnormality identification, determined spatial scattering and determined chromatic impact are each indicative of unhealthy tissue within the target area, the absorption amount is not determined. In one yet further embodiment, in the event that the determined chromatic impact and the determined absorption amount are each indicative of unhealthy tissue within the target area the output tissue information signal comprises an indication that grade 3 CIN (CIN3) is present within tissue under the surface of the target area, and wherein in the event that the determined chromatic impact is not indicative of unhealthy tissue within the target area and the determined absorption amount is indicative of unhealthy tissue within the target area the output tissue information signal comprises an indication that grade 2 CIN (CIN2) is present within tissue of the target area.

In one embodiment, in the event that the image abnormality identification is indicative of unhealthy tissue within the target area and one of the determined chromatic impact and the determined spatial scattering is not indicative of unhealthy tissue within the target area, the output tissue information signal comprises one of: an indication that cervical polyps are present within tissue of the target area; and an indication that a benign tumor is present within tissue of the target area. In another embodiment, in the event that the determined spatial scattering is not indicative of unhealthy tissue within the target area and the determined chromatic impact is indicative of unhealthy tissue within the target area, the control circuitry is further arranged to: repeat the image abnormality identification; and repeat the determination of spatial scattering, wherein the output tissue information signal is further responsive to the repeated image abnormality identification and the repeated determined spatial scattering.

In one embodiment, in the event that the image abnormality identification, the determined spatial scattering and the determined chromatic impact are each indicative of unhealthy tissue within the target area, the control circuitry is further arranged to determine if the target area image output by the at least one broad band light sensor is indicative of a cancerous tumor within tissue of the target area, in the event that the control circuitry determines that the target area image is indicative of the cancerous tumor the output tissue information signal comprises an indication that a cancerous tumor is present within tissue of the target area, and in the event that the control circuitry determines that the target area image is not indicative of the cancerous tumor the output signal comprises an indication that CIN3 is present within tissue of the surface of the target area. In another embodiment, the control circuitry is further arranged to: determine the correlation between the output image of the target area and an image of group B *streptococcus*; and output a correlation signal responsive to the correlation determination.

In one independent embodiment, a method of diagnosis of tissue disease is provided, the method comprising: receiving an output of at least one light sensor arranged to: sense a broad band light after interaction with a target area of an organ, the broad band light output by a broad band light source arranged to irradiate the target area of the organ; output an image of the target area responsive to the sensed broad band light; sense a narrow band light after interaction with the target area, the narrow band light output by a narrow band light source arranged to irradiate the target area; and output a signal responsive to the sensed narrow band light, receiving an output of a color sensor arranged to sense the broad band light after interaction with the target area, the broad band light source, narrow band light source, at least one light sensor and color sensor situated within a housing; identifying an abnormality in the received target area image responsive to one of the intensity and color of the received target area image; determining the spatial scattering of the narrow band light sensed by the at least one light sensor; determining the chromatic impact of the interaction of the broad band light with the target area, responsive to the broad band light sensed by the color sensor; and outputting a tissue information signal responsive to the image abnormality identification, determined spatial scattering and determined chromatic impact.

In one embodiment, the method further comprises determining the amount of absorption of the narrow band light within the target area responsive to the narrow band light sensed by the at least one light sensor, wherein the output tissue information signal is further responsive to the determined absorption amount. In another embodiment, the at least one light sensor comprises: an imager arranged to output the image of the target area; and a light sensor array arranged to output the signal responsive to the sensed narrow band light.

In one embodiment, the output narrow band light is a coherent narrow band light. In another embodiment, in the event that the determined spatial scattering of the sensed narrow band light is indicative of unhealthy tissue within the target area the method further comprises determining the amount of absorption of the narrow band light within the target area responsive to the narrow band light sensed by the at least one light sensor, wherein the output tissue information signal is further responsive to the determined absorption amount.

In one further embodiment, in the event that the determined absorption amount is not indicative of unhealthy tissue within the target area the method further comprises: repeating the image abnormality identifying; repeating the spatial scattering determining, wherein the output tissue information signal is further responsive to the repeated image abnormality identification and the repeated determined spatial scattering. In another further embodiment, in the event that the determined absorption amount is indicative of unhealthy tissue within the target area the output tissue information signal comprises an indication that cervical intraepithelial neoplasia (CIN) is present within tissue of the target area.

In one further embodiment, in the event that the image abnormality identification, spatial scattering and chromatic impact are each indicative of unhealthy tissue within the target area, the absorption amount is not determined. In one yet further embodiment, in the event that the determined chromatic impact and the determined absorption amount are each indicative of unhealthy tissue within the target area the output tissue information signal comprises an indication that grade 3 CIN (CIN3) is present within tissue under the surface of the target area, and wherein in the event that the determined chromatic impact is not indicative of unhealthy tissue within the target area and the determined absorption amount is indicative of unhealthy tissue within the target area the output tissue information signal comprises an indication that grade 2 CIN (CIN2) is present within tissue of the target area.

In one embodiment, in the event that the image abnormality identification is indicative of unhealthy tissue within the target area and one of the determined chromatic impact and the determined spatial scattering is not indicative of unhealthy tissue within the target area, the output tissue information signal comprises one of: an indication that cervical polyps are present within tissue of the target area; and an indication that a benign tumor is present within tissue of the target area. In another embodiment, in the event that the determined spatial scattering is not indicative of unhealthy tissue within the target area and the determined chromatic impact is indicative of unhealthy tissue within the target area, the method further comprises: repeating the image abnormality identifying; and repeating the spatial scattering determining, wherein the output tissue information signal is further responsive to the repeated image abnormality identification and the repeated determined spatial scattering.

In one embodiment, in the event that the image abnormality identification, the determined spatial scattering and the determined chromatic impact are each indicative of unhealthy tissue within the target area the method further comprises determining if the received target area image is indicative of a cancerous tumor within tissue of the target area, in the event that the target area image is indicative of the cancerous tumor the output tissue information signal comprises an indication that a cancerous tumor is present within tissue of the target area, and in the event that the target area image is not indicative of the cancerous tumor the output tissue information the output tissue information signal comprises an indication that CIN3 is present within tissue of the surface of the target area. In another embodiment, the method further comprises: determining the correlation between the received target area image and an image of group B *streptococcus*; and outputting a correlation signal responsive to the correlation determining.

Additional features and advantages of the invention will become apparent from the following drawings and description.

BRIEF DESCRIPTION OF THE DRAWINGS

For a better understanding of various embodiments of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIGS. 20A-20B illustrate high level schematic diagrams of a light sensor array exhibiting an opening;

FIG. 21A illustrates an image of a Group B *Streptococcus* (GBS) strain present in a birth canal;

DETAILED DESCRIPTION

Figure 1A:
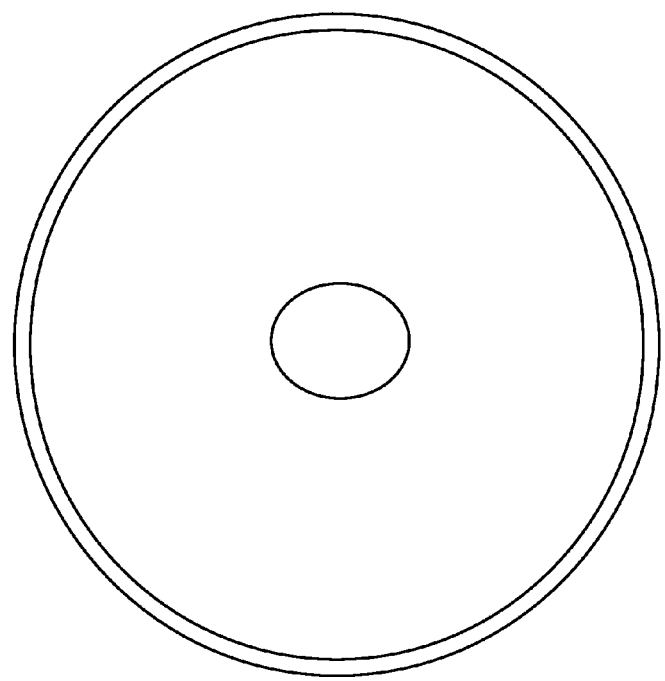
FIG. 1A schematically illustrates a computerized model of a healthy cell.

Before explaining at least one embodiment in detail, it is to be understood that the invention is not limited in its application to the details of construction and the arrangement of the components set forth in the following description or illustrated in the drawings. The invention is applicable to other embodiments being practiced or carried out in various ways. Also, it is to be understood that the phraseology and terminology employed herein is for the purpose of description and should not be regarded as limiting.

Figure 1B:
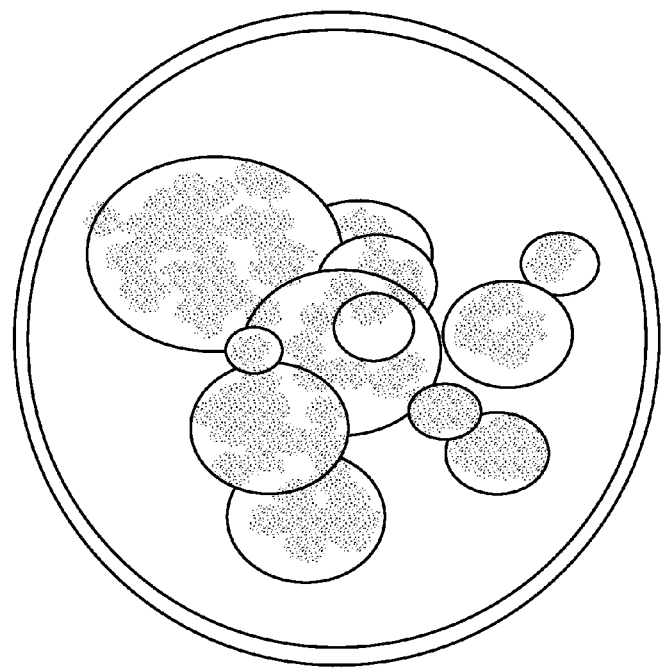
FIG. 1B schematically illustrates a computerized model of a cancerous cell.

A main difference between cervical cancer cells and normal cervical cells is their nuclear structure. Normal cells have a single nucleus, as shown in FIG. 1A, with a narrow range of sizes. The nucleus is generally round, oval or bean shaped. Pre-cancer and cancer cells have multiple nuclei, as shown in FIG. 1B, with a wide range of shapes and sizes. As a result, cancer cells scatter light by larger angles than healthy cells. Another reason for scattering of the light is the micro-structure of the nuclear-distribution of chlorine parts, enlargement of blood vessels and other characteristics.

Figure 2A:
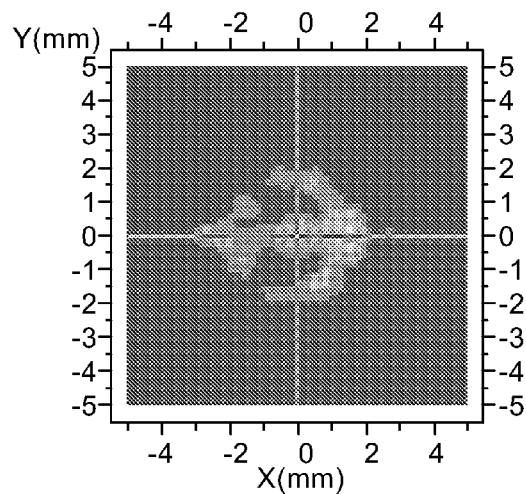
FIGS. 2A-2D illustrate the light spatial scattering properties of healthy tissue and cancerous tissue.
Figure 2B:
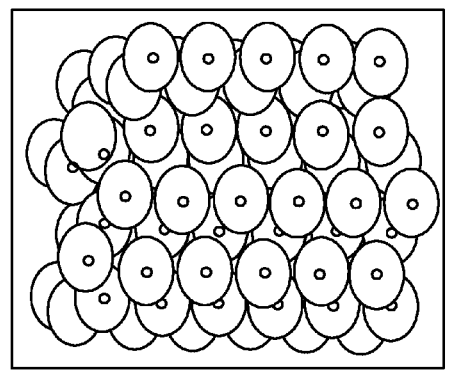
Figure 2C:
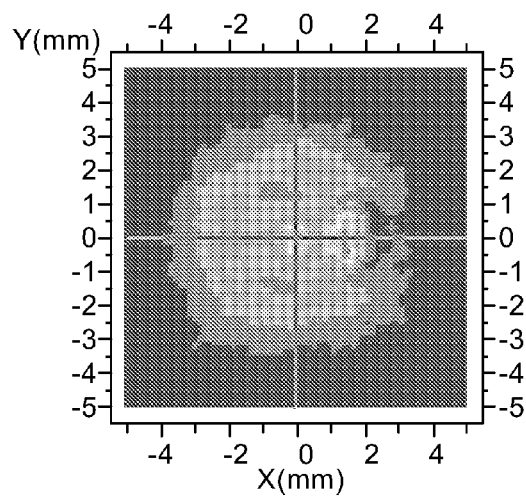
Figure 2D:
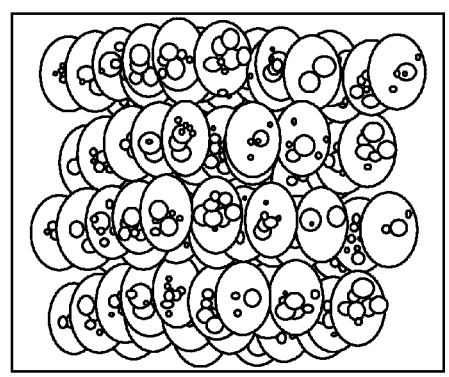

FIG. 2A illustrates a graph of the spatial scattering of a laser reflected off of tissue exhibiting healthy cells illustrated in FIG. 2B, the x-axis and y-axis representing the dimensions of the received light in millimeters; and FIG. 2C illustrates a graph of the spatial scattering of a laser reflected off of tissue exhibiting cancerous cells illustrated in FIG. 2D, the x-axis and y-axis representing the dimensions of the received light in millimeters. In both FIGS. 2A and 2C the laser penetrates the respective tissue to a depth of 120 um. As will be described below, a method of determining the spatial scattering of light after interaction with the tissue can be indicative of unhealthy tissue.

Figure 3:
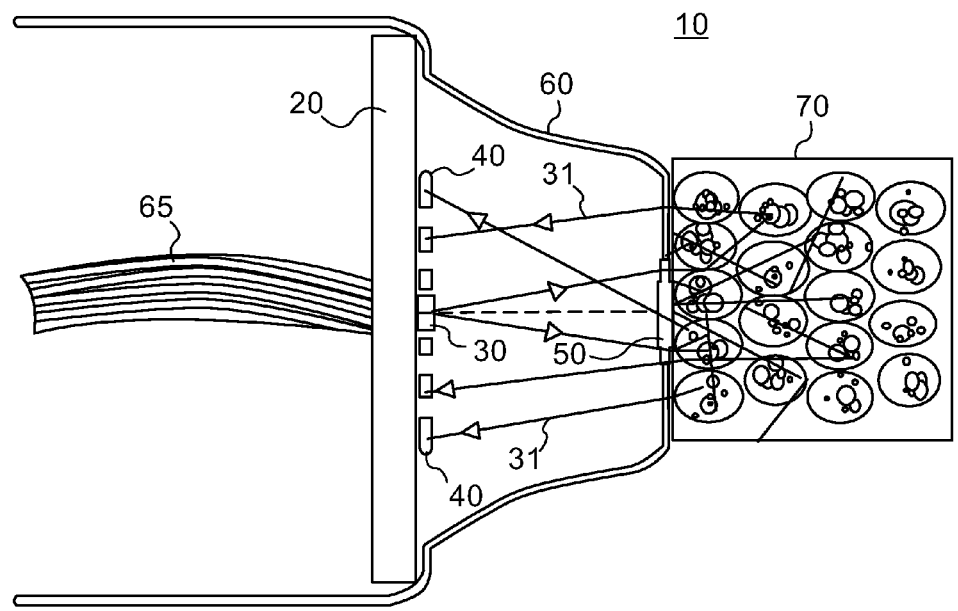
FIG. 3 illustrates a high level schematic diagram of a light scattering determination unit, according to certain embodiments.

FIG. 3 illustrates a high level schematic diagram of a light scattering determination unit 10 arranged to determine the light spatial scattering properties of tissue. Light scattering determination unit 10 comprises: a printed circuit board (PCB) 20; a narrow band light source 30; a light sensor array 40; a collimating lens 50; a cover 60; and data cable 65. In one embodiment, narrow band light source 30 comprises a coherent monochromatic narrow band light source such as a laser. In one further embodiment, narrow band light source 30 is arranged to output a vertical structure coherent light. In another further embodiment, narrow band light source 30 comprises a vertical-cavity surface-emitting laser (VCSEL), such as 3 mW Single-Mode 950 nm VCSEL chip Part# PSM-BC-003-W0950 commercially available from Princeton Optronics, Inc. of Mercerville, N.J. In one embodiment, narrow band light source 30 and light sensor array 40 are implemented on PCB 20. In one embodiment, collimating lens 50 is part of cover 60. In one embodiment, light sensor array comprises one or more of a PIN sensor array and an avalanche photo diode (APD) sensor array. In one exemplary embodiment, light sensor array 40 comprises an A1312I image sensor commercially available from Photonfocus AG of Bahnhofplatz, Switzerland.

In operation, narrow band light source 30 generates a narrow band light 31, which is focused by collimating lens 50 to irradiate a target area 70 of an organ, optionally a cervix. The term "target area" as used in the present disclosure is defined as at least the surface layer of an area of an organ. The target area may additionally include subsequent layers of the organ or may extend into the depth of the organ. Narrow band light 31 is scattered by the cells of target area 70 and at least a portion of the returned narrow band light 31 is detected by light sensor array 40. Light sensor array 40 outputs signals corresponding to the returned light to a control circuitry (not shown) for further processing.

Light sensor array 40 transfers the signals to a computer system, such as a Personal Computer (PC) or other suitable computer based system capable of executing a processing program, via data cable 65. In one embodiment, the processing program calculates the ratio between the intensity of light detected by one or more sensors positioned in the center of light sensor array 40 and the intensity of light detected by one or more sensors removed from the center of light sensor array 40. In one further embodiment, the ratio between an average of the intensity of light detected by a plurality of sensors positioned in the center of light sensor array 40 and an average of the intensity of light detected by a plurality of sensors removed from the center of light sensor array 40 is calculated. In the event that the determined ratio is greater than a predetermined scattering threshold, the control circuitry outputs a tissue information signal indicative of unhealthy tissue cells of target area 70. In one embodiment, the range or value of the predetermined scattering threshold is determined responsive to in-vivo measurements of fluids and other matter present in the vicinity of target area 70. In another embodiment, the processing program calculates the ratio between the number of "lit" pixels representing light, i.e. the pixels which received the reflected narrow band light 31, in one or more sensors positioned in the center of light sensor array 40 and the number of "lit" pixels representing light in one or more sensors removed from the center of light sensor array 40. Optionally, a pixel is considered "lit" only in the event that the reflected narrow band light 31 received thereby exhibits an intensity greater than a predetermined minimum.

In another embodiment (not shown), light sensor array 40 is replaced with an imager, such as a charge coupled device (CCD), as will be described below in relation to FIG. 4.

Unless otherwise indicated, the functions described herein with respect to the processing program may be performed by an executable code and instructions stored in computer readable medium and running on one or more processor-based systems (e.g., a PC), however this is not meant to be limiting. In another embodiment, state machines, and/or hardwired electronic circuits can also be utilized. Additionally, with respect to the processes described herein, not all of the process states need to be reached, nor do the states have to be performed in the illustrated order. Furthermore, certain process states that are illustrated as being serially performed can be performed in parallel.

Figure 4:
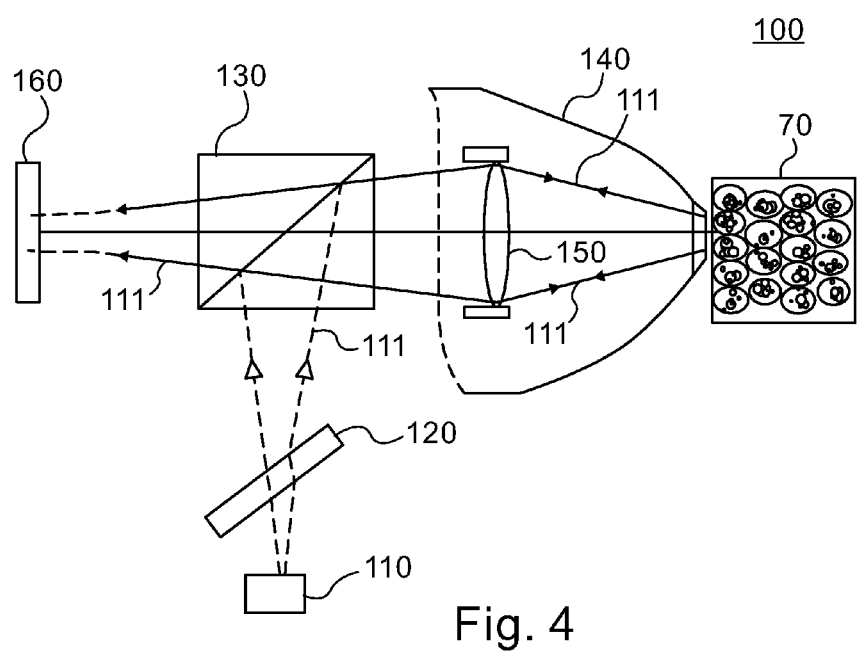
FIG. 4 illustrates a high level schematic diagram of an imaging unit, according to certain embodiments.

FIG. 4 illustrates a high level schematic diagram of an imaging unit 100, according to certain embodiments. Imaging unit 100 comprises: a broad band light source 110 (for example white LED FCW3200Z from Seoul semiconductor) arranged to emit a broad band light 111; an astigmatic element 120, such as a cylindrical lens or tilted plate; a beam splitter 130; a cover 140; an objective lens 150; and a light sensor 160. In one embodiment, broad band light source 110 comprises an LED, such as white LED FCW300Z commercially available from Seoul Semiconductor Co., Ltd. of Gyeonggi-do, Korea. In one embodiment, light sensor 160 is an imager such as a CCD or complementary metal-oxide semiconductor (CMOS) sensor.

In operation, broad band light 111 is output by broad band light source 110. Output broad band light 111 passes through astigmatic element 120. Broad band light 111 is reflected by beam-splitter 130 and focused by objective lens 150 onto target area 70 of the examined organ. In one embodiment, cover 140 is in contact with target area 70. Broad band light 111 is then reflected by target area 70 towards light sensor 160 through cover 140, objective lens 150 and beam-splitter 130. The reflected broad band light 111 is sensed by light sensor 160 and the image information of target area 70 is output to a control circuitry (not shown). In one embodiment, the image data is further output to a display (not shown) and an image of target area 70 is shown on the display.

After the image of target area 70 is captured by light sensor 160, it is output to the control circuitry and processed with an image processing algorithm to identify an abnormality in the image responsive to one of intensity and color of the image. In one embodiment, the image abnormality represents a disuniformity of the image. In one embodiment, the image abnormality identification comprises the following steps:

1. Determining the intensity distribution of the image output by light sensor 160, optionally the image is a grayscale image.
2. Determining the pixel exhibiting the greatest intensity value, the value denoted Imax. Optionally, Imax is selected only if at least a predetermined number of pixels exhibit an intensity within a predetermined range of Imax.
3. Determining the pixel exhibiting the lowest intensity value, the value denoted Imin. Optionally, Imin is selected only if at least a predetermined number of pixels exhibit an intensity within a predetermined range of Imin.
4. Determining the average of Imin and Imax, the average denoted Imedium.
5. Determining the number of pixels which exhibit an intensity greater than Imedium, the determined number of pixels denoted Sgreat.
6. Determining the number of pixels which exhibit an intensity greater than Imedium, the determined number of pixels denoted Sless.
7. Determining the ratio between Sgreat and Sless.
8. In the event that the determined ratio is greater than a predetermined intensity ratio level, an image abnormality is identified and the control circuitry is arranged to output a tissue information signal indicative of unhealthy tissue, i.e. there are abnormal cells within target area 70.

Another embodiment of the arrangement of the control circuitry to identify an image abnormality will be described below in relation to FIGS. 13-14.

Preferably, for each patient a new cover 140 should be used for hygienic reasons. However, different covers have slight differences in thickness due to manufacturing tolerances; therefore refocusing of the optical system should be done after replacing the cover, as will be described below. Additionally, there might be a difference between the operators in pulling the cover all the way down.

Figure 5:
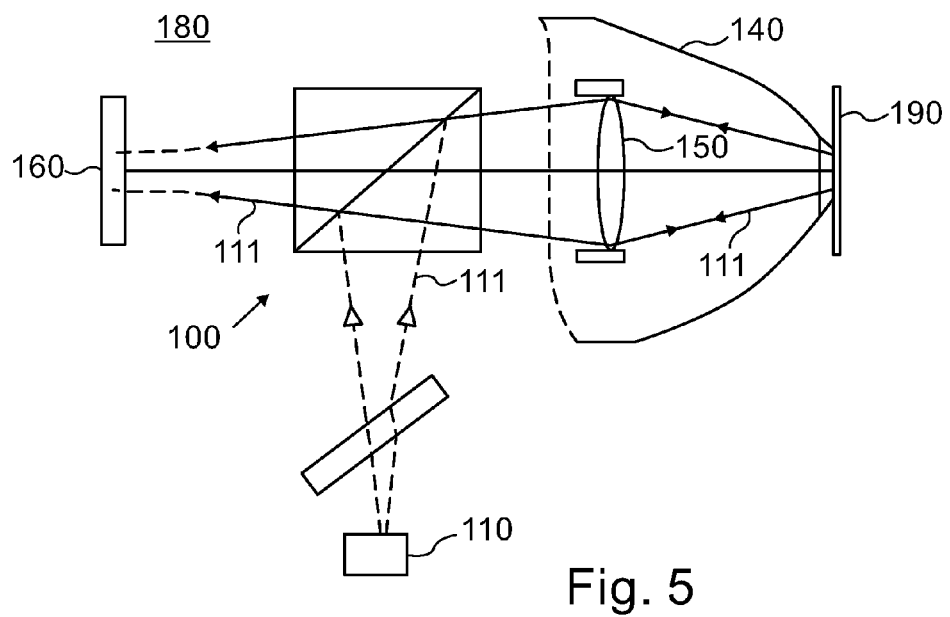
FIGS. 5-8 illustrate a focusing system for the imaging unit of FIG. 4, according to certain embodiments.
Figure 6:
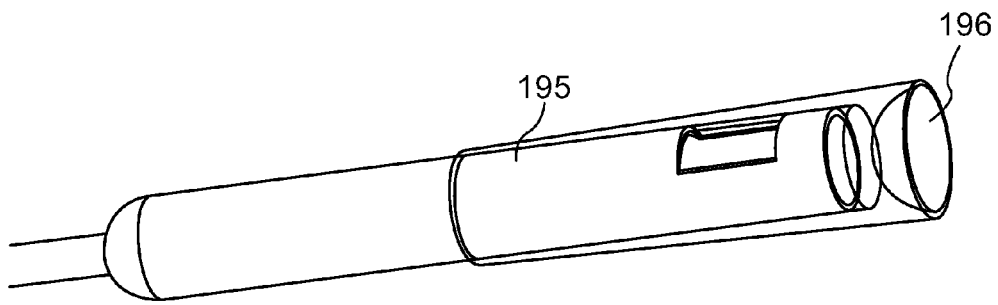
Figure 7A:
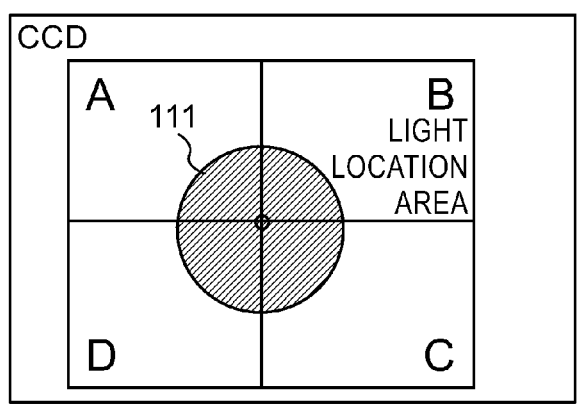
Figure 7B:
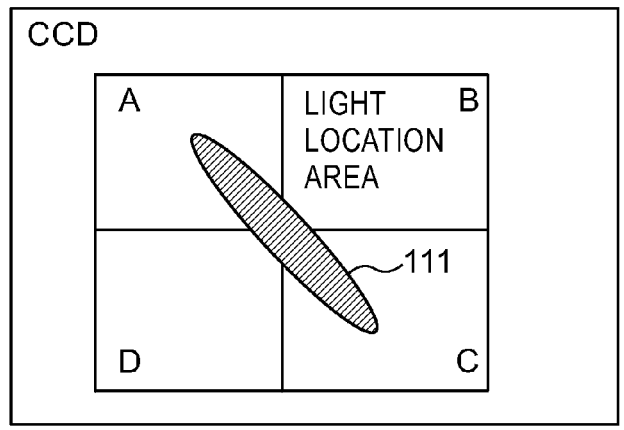
Figure 7C:
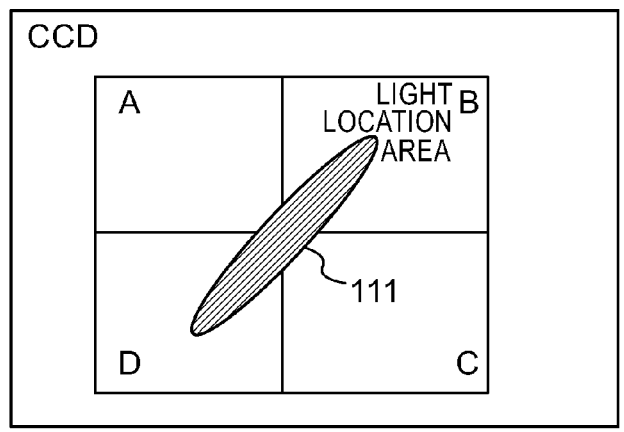
Figure 8:
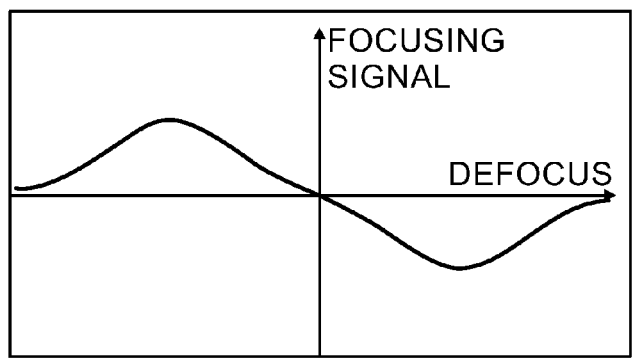

FIGS. 5 and 6 illustrate a schematic diagram of an arrangement 180 for focusing of imaging unit 100 of FIG. 4, according to certain embodiments, the figures being described together. Arrangement 180 comprises: imaging unit 100; a mirror 190; and a jacket 195. Jacket 195 exhibits a cervix attachment member 196 arranged to be attached to the cervix during operation, as will be described below in relation to FIG. 16. In one embodiment (not shown), objective lens 150 of imaging unit 100 is in communication with a translation mechanism (not shown), such as a servomotor, arranged to adjust the position of objective lens 150, as will be described further below. Focusing of imaging unit 100 is done before deployment within the vagina. The outer surface of cover 140 is in contact with mirror 190 and imaging unit 100, along with mirror 190, are placed within jacket 195. When imaging unit 100 is focused, the broad band light 111 reflected off of mirror 190 exhibits a round shape on light sensor 160, as shown in FIG. 7A. When imaging unit 100 is out of focus, the broad band light 111 reflected off of mirror 190 exhibits an elliptical shape, as shown in FIGS. 7B-7C, the elliptical orientation depending on the defocusing direction of imaging unit 100. The defocusing direction of imaging unit 100 is illustrated by the graph of FIG. 8, where the x-axis represents the defocusing direction and the y-axis represents a focusing signal. In particular, the x-axis coordinate of each point of the focusing signal indicates how "out of focus" a particular lens is and in which direction. It is to be noted that the focusing signal is not an injective function and more than one coordinate on the focusing signal may exhibit the same y-axis value and yet exhibit different x-axis values. In particular, in one illustrated embodiment the focusing signal is generally "S" shaped.

In operation, and as described above, broad band light source 110 is arranged to irradiate target area 70 with broad band light 111 and broad band light 111 is reflected back to light sensor 160. The information received by light sensor 160 is output to the control circuitry and the control circuitry is arranged to perform a focusing algorithm. The focusing algorithm comprises the following steps:

1. Determining the light location area on light sensor 160, i.e. the area where the reflected broad band light 111 is received by light sensor 160. In one embodiment, the light location area is determined by employing an edge detection algorithm.
2. Determining the coordinates of the center point of the light location area.
3. Defining a border area surrounding the light location area, where the determined center point coordinates of the light location area define the coordinates of the center point of the border area.
4. Dividing the defined border area into four equal parts, denoted A, B, C and D, thus creating a virtual quadrant detector, as shown in FIGS. 7A-7C.
5. Calculating the number of pixels in each part, the number of pixels representing the amount of light in each part and denoted SA, SB, SC and SD respectively for each of parts A, B, C and D.
6. Calculating a focusing signal value, denoted FS, of the light location area according to the equation:

$$FS=[(SA+SC)-(SB+SD)]/[SA+SC+SB+SD] \qquad \text{EQ. 1}$$

where, as described above, the focusing signal value FS is the coordinate on the focusing signal of FIG. 8 which the x-axis value thereof represents how out of focus objective lens 150 is with mirror 190.

7. Adjusting the position of objective lens 150 such that focusing signal value FS will equal zero.

Figure 9:
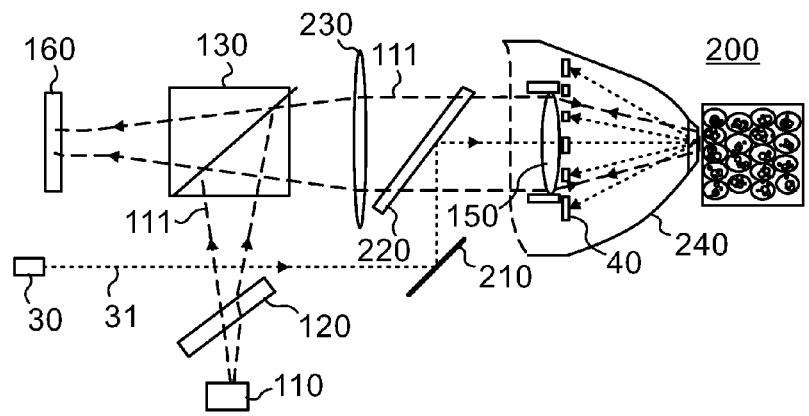
FIG. 9 illustrates a high level schematic diagram of a tissue disease diagnosis apparatus implementing light scattering determination unit of FIG. 3 and imaging unit of FIG. 4, according to certain embodiments.

FIG. 9 illustrates a high level schematic diagram of a tissue disease diagnosis apparatus 200, according to certain embodiments. Tissue disease diagnosis apparatus 200 combines light scattering determination unit 10 of FIG. 3 and imaging unit 100 of FIG. 4, as will be described below. Tissue disease diagnosis apparatus 200 comprises: a narrow band light source 30; a light sensor array 40; a mirror 210; a beam splitter 220; a collimating lens 230; a cover 240; a broad band light source 110; an astigmatic element 120; a beam splitter 130; an objective lens 150; and a light sensor 160.

In operation, a narrow band light 31, optionally a coherent narrow band light, is output by narrow band light source 30, as described above. The output narrow band light 31 is reflected by mirror 210 to beam splitter 220. Beam splitter 220 reflects narrow band light 31 to objective lens 150 and from there through light sensor array 40 and cover 240 to irradiate a target area 70 of a cervix. In one embodiment, light sensor array 40 is semi-transparent thereby allowing the output narrow band light to pass there through. In another embodiment, light sensor array 40 exhibits holes sufficiently large to allow light to pass through, as will be described below in relation to FIGS. 19-20B. As described above, the scattered narrow band light 31 is detected by light sensor array 40 and a control circuitry is arranged to determine if there is unhealthy tissue within target area 70.

As described above in relation to imaging unit 100, broad band light source 110 is arranged to output a broad band light 111. Broad band light 111 passes through astigmatic element 120 and is reflected by beam-splitter 130 through collimating lens 230, beam-splitter 220, and objective lens 150. Objective lens 150 focuses broad band light 111 through light sensor array 40 and cover 240 to irradiate target area 70. In one embodiment, as described above, cover 240 is in contact with target area 70. Broad band light 111 is then reflected from target area 70 through cover 240, light sensor array 40, objective lens 150, beam splitter 220, collimating lens 230 and beam splitter 130 to be received by light sensor 160. As described above, light intensity information of the received broad band light 111 is output to a control circuitry which is arranged to determine if target area 70 exhibits unhealthy tissue.

Figure 10:
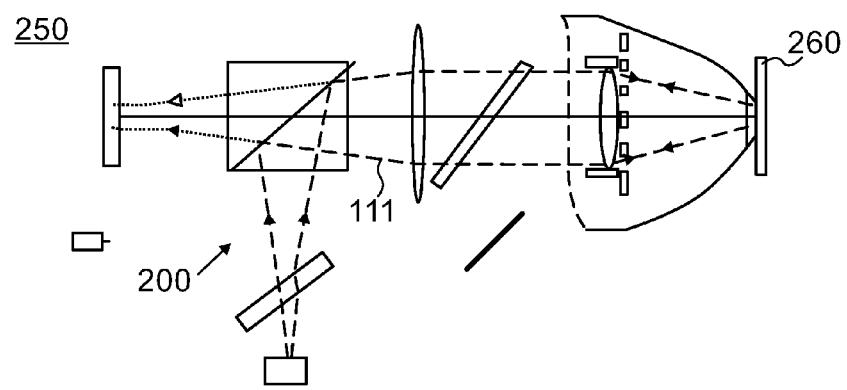
FIG. 10 illustrates a high level schematic diagram of a focusing system for the tissue disease diagnosis apparatus of FIG. 9.

FIG. 10 illustrates a schematic diagram of an arrangement 250 for focusing tissue disease diagnosis apparatus 200, comprising tissue disease diagnosis apparatus 200 and a mirror 260. As described above in relation to arrangement 180 for focusing imaging 100, broad band light 111 is reflected off mirror 260 to determine how focused objective lens 150 is.

Figure 11A:
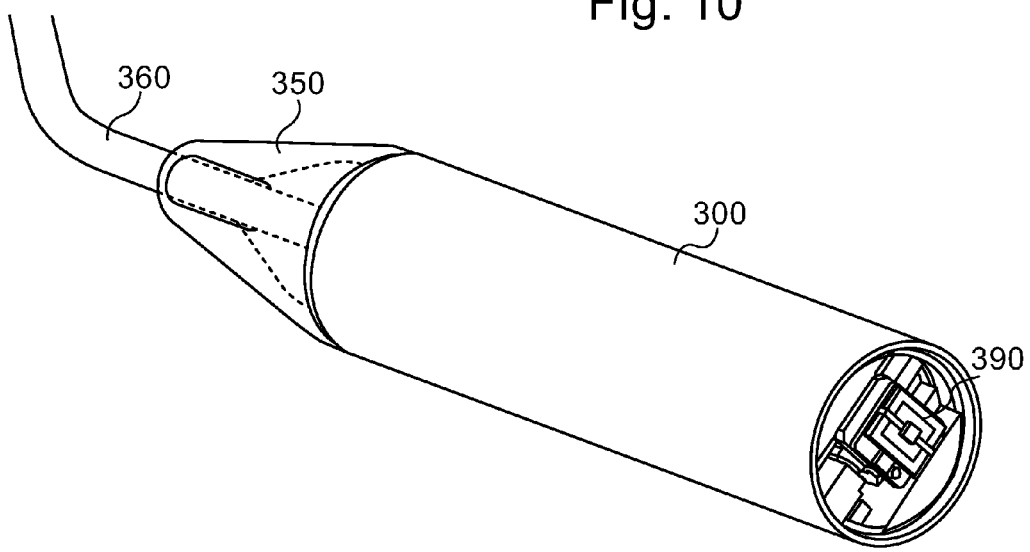
FIGS. 11A-11C illustrate a high level schematic diagram of a probe for use with the tissue disease diagnosis apparatus of FIG. 9, according to certain embodiments.
Figure 11B:
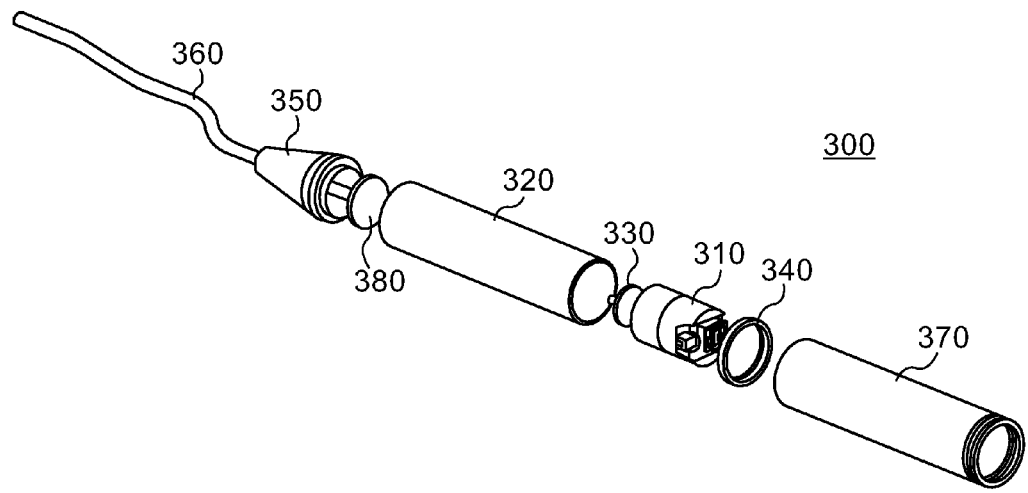
Figure 11C:
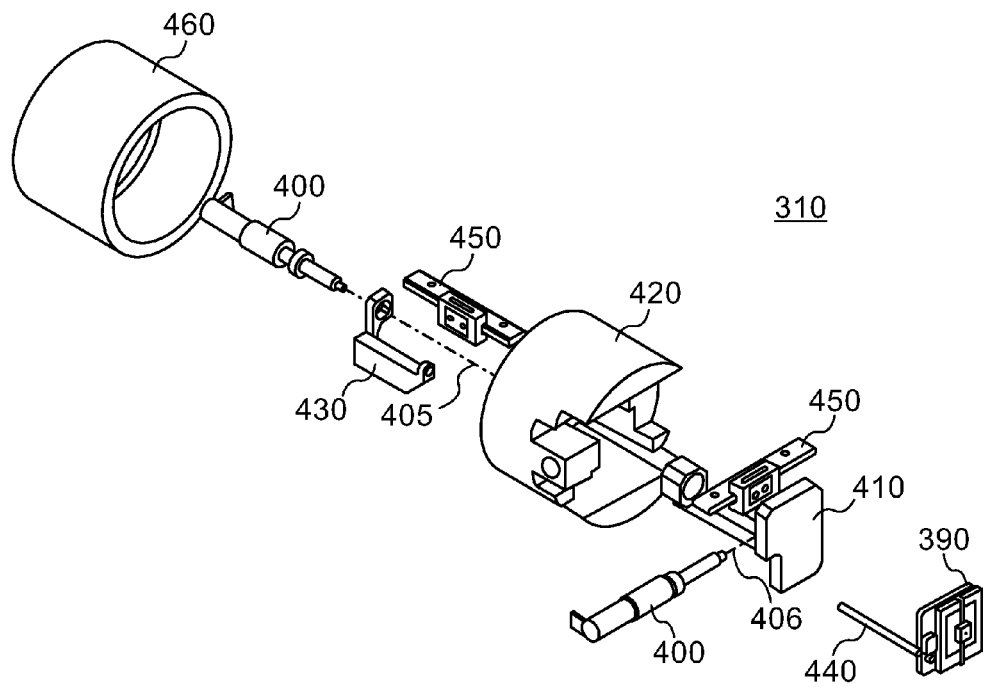

FIG. 11A illustrates a perspective view of a probe 300 for use with apparatus 200 of FIG. 9, according to certain embodiments; and FIGS. 11B-11C illustrate perspective views of various components of probe 300, the figures being described together. As illustrated in FIG. 11B, probe 300 comprises: a linear stage sub assembly (LSSA) 310; a housing 320, optionally tubular shaped; a motor 330; a front window 340, optionally ring shaped; a back cover 350, optionally cone shaped; a data cable 360; a jacket 370, optionally tubular shaped; and an electronic interface card 380. As illustrated in FIG. 11C, LSSA 310 comprises: an optical sub assembly 390; a first and second linear actuator 400, such as series 03A S3 linear actuator in combination with a series 0308A brushless DC motor exhibiting a maximum force of 2.87 N, commercially available from Faulhaber Minimotor of Croglio Switzerland; a linear stage base 410; a linear stage housing 420; a bracket 430; a camera 440; a first and second linear slide 450, such as an IKO linear slide LWL 1-Y-1, 18-3-25 LWL 1-Y-1-18-3-25 precision grade "H", commercially available from Nippon Thompson Co., Ltd. of Tokyo, Japan; and a linear stage housing gear interface 460. LSSA 310 is illustrated in FIG. 11C as comprising a camera 440, however this is not meant to be limiting in any way and a different type of broad band light source and light sensor may be provided as described above in relation to imaging unit 100 of FIG. 4. As will be described below in relation to FIG. 12, LSSA 310 comprises additional components not illustrated in FIG. 11C.

Camera 440 is situated within an opening of optical sub assembly 390 and optical sub assembly 390 is arranged to be in contact with linear stage base 410. Linear stage base 410 is in mechanical communication with first linear actuator 400, first linear slide 450 and linear stage housing 420. Bracket 430 is in mechanical communication with second linear actuator 400, second linear slide 450 and linear stage housing 420. A first end of linear stage housing gear interface 460 is in communication with linear stage housing 420 and a second end of linear stage housing gear interface 460 is in communication with motor 330 of FIG. 11B. Front window 340 is positioned to surround optical sub assembly 390 and motor 330 is in communication with electronic interface card 380. Electronic interface card 380 is in communication with data cable 360 and data cable 360 is in communication with an external system (not shown). LSSA 310, motor 330 and electronica interface card 380 are situated within housing 320 and an end of housing 320 is in contact with back cover 350, data cable 360 arranged to extend through an opening within back cover 350. Housing 320 and back cover 350 are situated within jacket 370. In operation, first and second linear actuators 400 are arranged to translate optical sub assembly 390 across orthogonal axes 405 and 406 and motor 330 is arranged to rotate linear stage housing gear interface 460 and linear stage housing 420 around axis 405.

Figure 12:
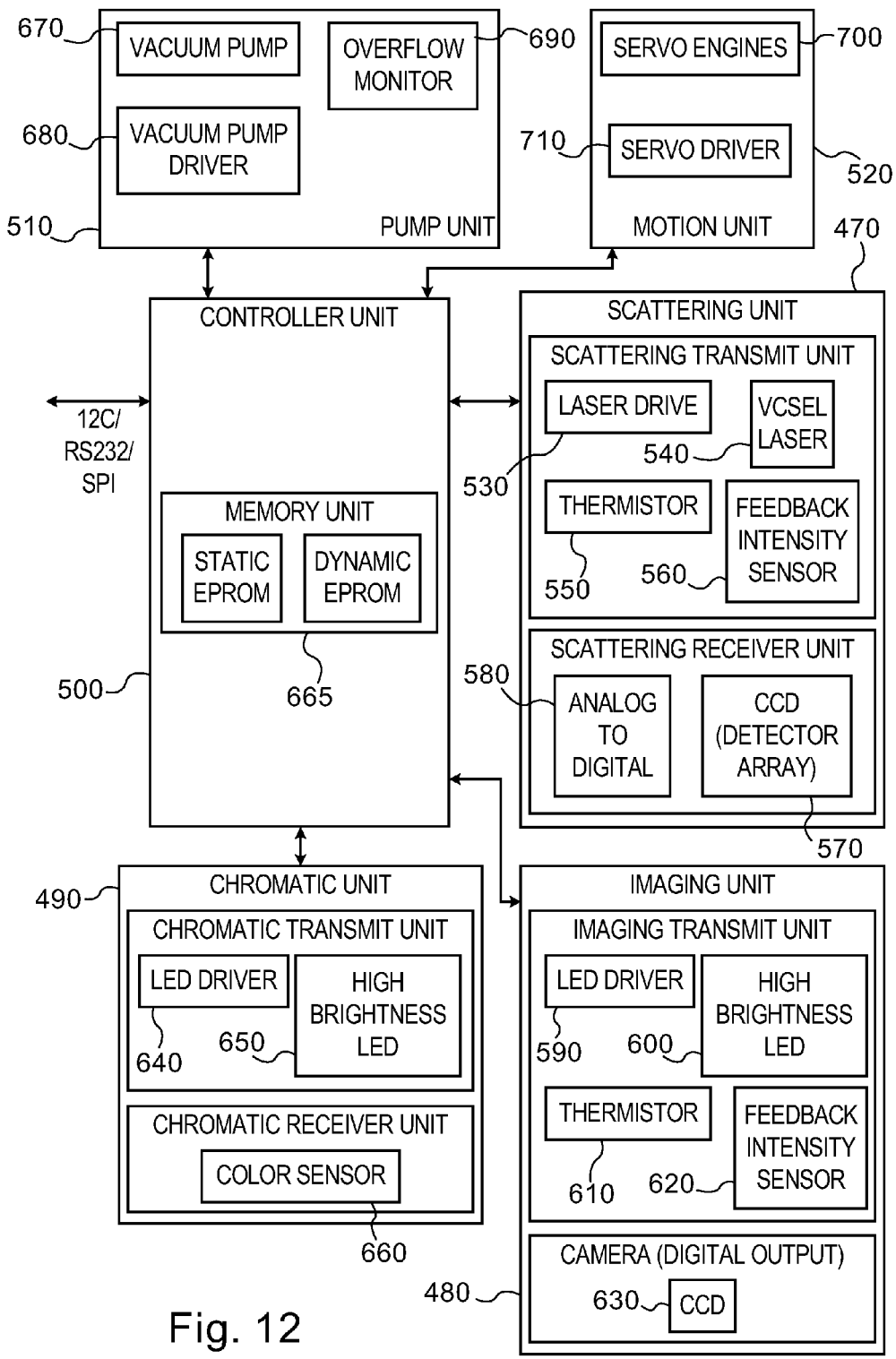
FIG. 12 illustrates a block diagram of a Linear Stage Sub Assembly (LSSA) that drives and carries the optical system of the probe of FIGS. 11A-11C device, according to certain embodiments.

FIG. 12 illustrates, in a block diagram form, the main elements of LSSA 310, according to certain embodiments. In particular, LSSA 310 comprises: a light scattering determination unit 470; an imaging unit 480; a chromatic impact determination unit 490; a controller unit 500; a pump unit 510; and a motion unit 520. Light scattering determination unit 470 comprises: a narrow band coherent light source driver 530, optionally a laser driver; a narrow band coherent light source 540, optionally a VCSEL laser; a thermistor 550; a feedback intensity sensor 560; a light sensor 570, optionally a light sensor array or a camera, as described above in relation to light scattering determination unit 10 of FIG. 3; and an analog to digital converter (ADC) 580. Imaging unit 480 comprises: a broad band light source driver 590, optionally an LED driver; a broad band light source 600, optionally a high brightness white LED; a thermistor 610; a feedback intensity sensor 620; and a light sensor 630, optionally a CCD or CMOS light sensor such as a camera. Chromatic impact determination unit 490 comprises: a broad band light source driver 640, optionally an LED driver; a broad band light source 650, optionally a high brightness white LED; and a color sensor 660. Control unit 500 is in one embodiment implemented as a microcontroller or microprocessor and comprises a memory unit 665 optionally comprising a static and dynamic erasable programmable read only memory. Pump unit 510 comprises: a vacuum pump 670; a vacuum pump driver 680; and an overflow monitor 690. Motion unit 520 comprises: a plurality of servo engines 700; and a plurality of servo drivers 710.

In operation, control unit 500 is arranged to control light scattering determination unit 470, imaging unit 480, chromatic impact determination unit 490, pump unit 510 and motion unit 520. Laser driver 530 of light scattering determination unit 470 is arranged to drive laser 540 and thermistor 550 and feedback intensity sensor 560 are arranged, in cooperation with control unit 500 to control the intensity of the output light of laser 540. As described above in relation to light scattering determination unit 10, light sensor 570 is arranged to receive the output laser after interaction with a target area and ADC 580 is arranged convert the received information into digital format, the digital information being output to control unit 500 for further processing.

LED driver 590 of imaging unit 480 is arranged to drive LED 600, and thermistor 610 and feedback intensity sensor 620 are arranged, in cooperation with control unit 500, to control the intensity of the output light of LED 600. As described above in relation to imaging unit 100, CCD 630 is arranged to receive the output light after interaction with a target area the received information being output to control unit 500 for further processing.

As will be described below in relation to FIGS. 17-18, led driver 640 of chromatic impact unit 490 is arranged to drive LED 650. As will be described below, color sensor 660 is arranged to receive the output light after interaction with a target area, the received information being output to control unit 500 for further processing. In one embodiment a separate LED 650 is not provided, rather the light output by LED 600 is sensed by both camera 630 and color sensor 660. Vacuum pump driver 680 of pump unit 510 is arranged to drive vacuum pump 670 to extract in-vivo fluids and to improve the contact between the inserted probe and the cervix, and overflow monitor 690 is arranged to monitor the amount of fluids extracted by vacuum pump 670 so as not to overload vacuum pump 670. Each servo driver 710 of motion unit 520 is arranged to drive a particular servo engine 700. Servo engines 700 are arranged to translate the optical units, responsive to the control circuitry, for better positioning as described above. Memory unit 665 is arranged to store thereon the received information from light scattering determination unit 470, imaging unit 480 and chromatic impact determination unit 490 and further have stored thereon information regarding the control of the different units. In one embodiment, control unit 500 is in communication with an external control circuitry, which is arranged to process the information received from each of light sensor 570, light sensor 630 and color sensor 660 and in another embodiment control unit 500 is arranged to process the information.

Figure 13A:
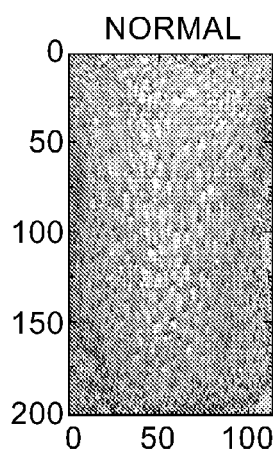
FIGS. 13A-13H illustrate images and 2-dimensional Fourier transforms of various tissues.
Figure 13C:
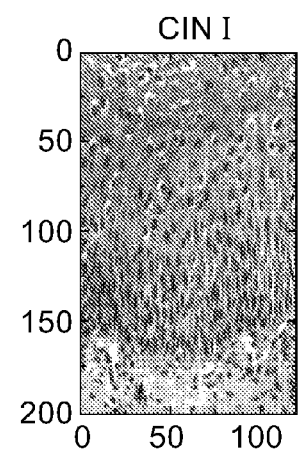
Figure 13B:
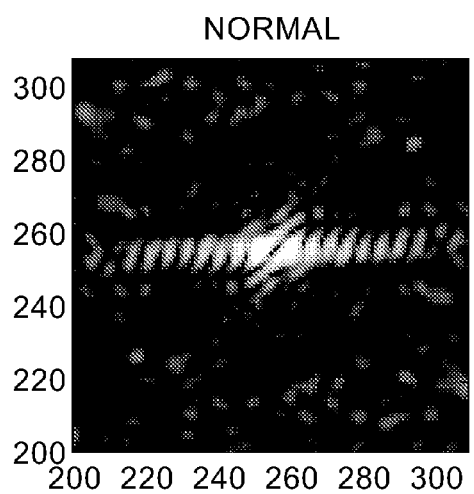
Figure 13D:
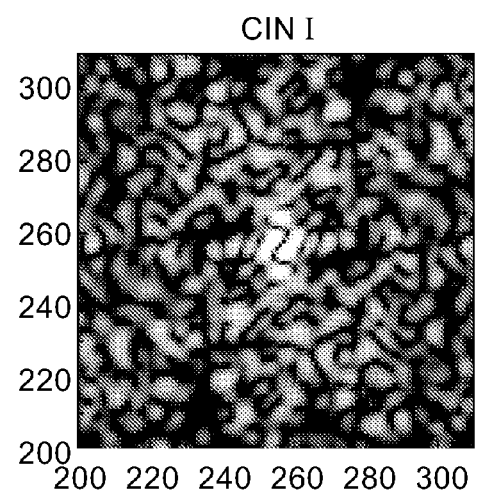
Figure 13E:
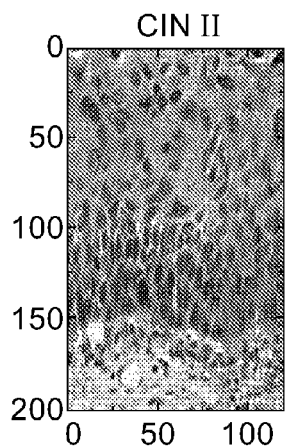
Figure 13G:
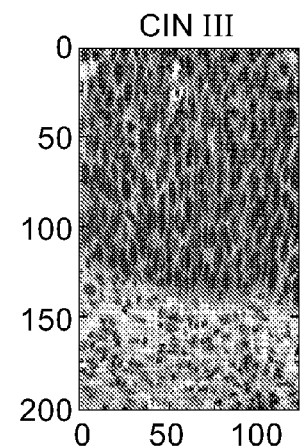
Figure 13F:
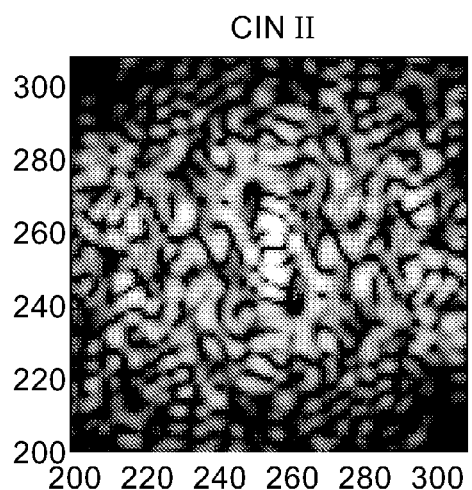
Figure 13H:
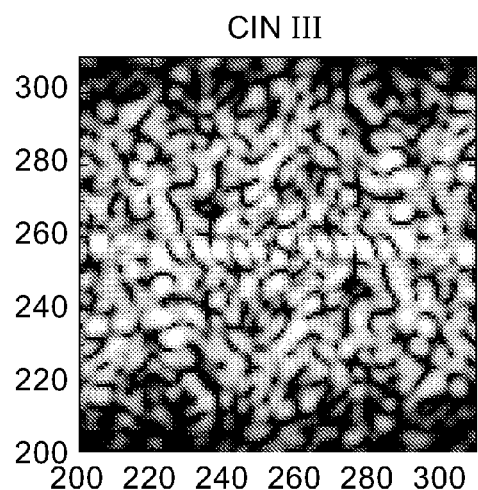
Figure 14:
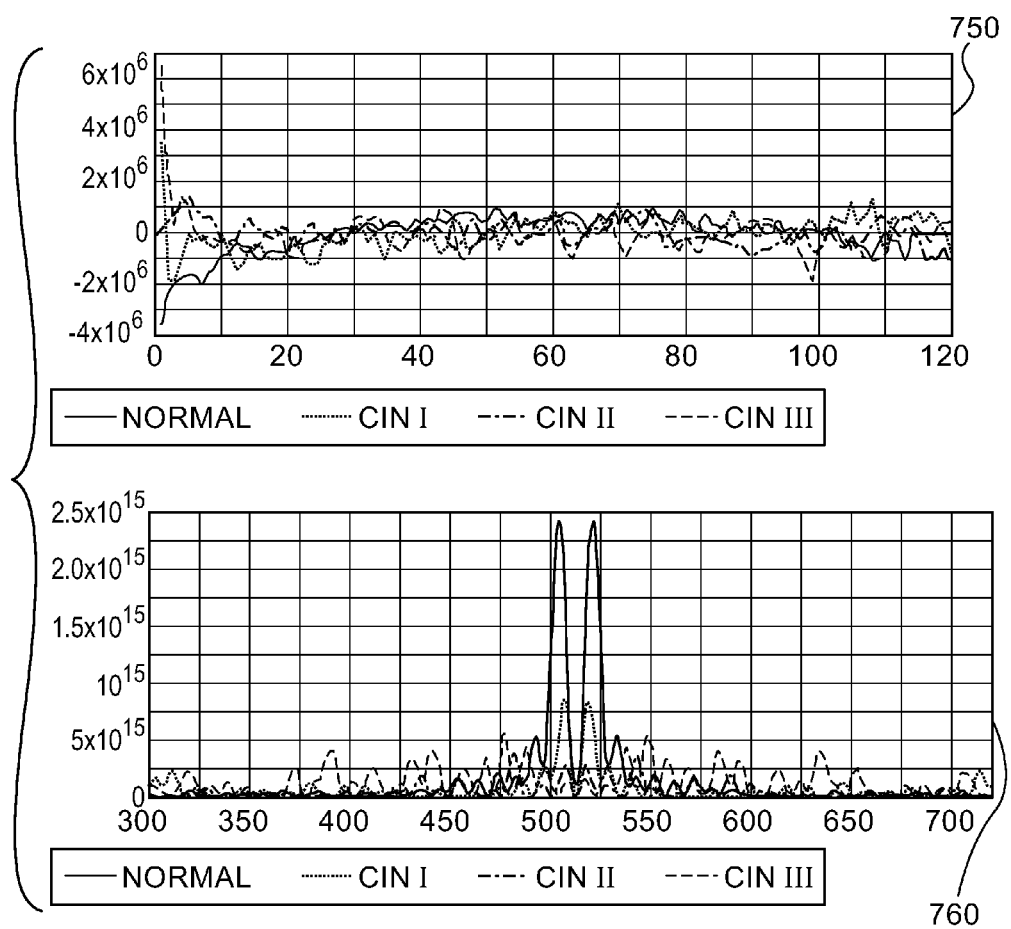
FIG. 14 illustrates the Fourier transform of the imaged tissues of FIGS. 13A-13H.

FIGS. 13A-13H illustrate various images of cervical tissue and a 2 dimensional Fourier transform of the images, and FIG. 14 illustrates graphs of the method of performing the Fourier transform so as to identify an image abnormality, the figures being described together. In particular, FIGS. 13A, 13C, 13E and 13G are images of the cervical tissue after hematoxylin and eosin (H&E) staining. In one embodiment, as described above in relation to imaging unit 100 of FIG. 4, a broad band light 111 is received by a light sensor 160 which is arranged to output the image of target area 70. In one embodiment, light sensor 160 comprises a high resolution camera, such as the MO-T1003L-60 commercially available from Misumi Electronics Corp. of New Taipei City, Taiwan. FIG. 13A shows normal cervical tissue, FIG. 13C shows tissue exhibiting grade 1 cervical intraepithelial neoplasia (CIN1), FIG. 13E shows tissue exhibiting grade 2 cervical intraepithelial neoplasia (CIN2) and FIG. 13G shows tissue exhibiting grade 3 cervical intraepithelial neoplasia (CIN3).

FIG. 14 illustrates a graph 750 of a mean of a portion of each of the images of FIGS. 13A, 13C, 13E and 13G in the vertical direction, where the x-axis represents the area of the image and the y-axis represents the mean in the vertical direction. In particular, the line designated as normal is the mean of a portion of the image of FIG. 13A, the dotted line designated as CIN I is the mean of a portion of the image of FIG. 13C, the dashed line designated as CIN II is the mean of a portion of the image of FIG. 13E and the dashed line designated as CIN III is the mean of a portion of the image of FIG. 13G. Graph 760 of FIG. 14 illustrates a Fourier transform of the means of graph 750 in the frequency domain. FIG. 13B shows an image of the 2 dimensional Fourier transform of the tissue of FIG. 13A illustrated in graph 760, FIG. 13D shows an image of the 2 dimensional Fourier transform of the tissue of FIG. 13C illustrated in graph 760, FIG. 13F shows an image of the 2 dimensional Fourier transform of the tissue of FIG. 13E illustrated in graph 760, and FIG. 13H shows an image of the 2 dimensional Fourier transform of the tissue of FIG. 13G illustrated in graph 760. As shown, the more white that shows up on the black background the more severe the condition of the tissue. In particular, as seen in graph 760, for normal tissue the Fourier transform exhibits a large main lobe in the lower frequencies compared to the higher frequencies. For the images of unhealthy tissue, such as the tissue of FIG. 13G exhibiting CIN3, the main lobe of the lower frequencies is only a small fraction of the frequencies of the transform. As described above, the control circuitry is arranged to identify an image abnormality responsive to one of intensity and color of the image. Thus, the control circuitry is arranged to identify an image abnormality responsive to the determined Fourier transform. In one embodiment, in the event that the ratio between the high frequency intensities and the low frequency intensities is greater than a predetermined frequency ratio threshold the control circuitry is arranged to output a tissue information signal indicating that unhealthy tissue is present within target area 70.

Table 1 illustrates the results of the image processing algorithm described above in relation to FIG. 4 on the tissues of FIGS. 13A, 13C, 13E and 13G.

TABLE 1

| Figure | Diagnosis | Ratio |
| --- | --- | --- |
| 13A | Normal | 0.77 |
| 13C | CIN1 | 3.06 |
| 13E | CIN2 | 6.25 |
| 13G | CIN3 | 19.71 |

In particular, the ratio between Sgreat and Sless, as described above, is shown for the tissue of each figure. As shown by table 1, the more severe the condition of the tissue is, the greater the ratio is.

Figure 15:
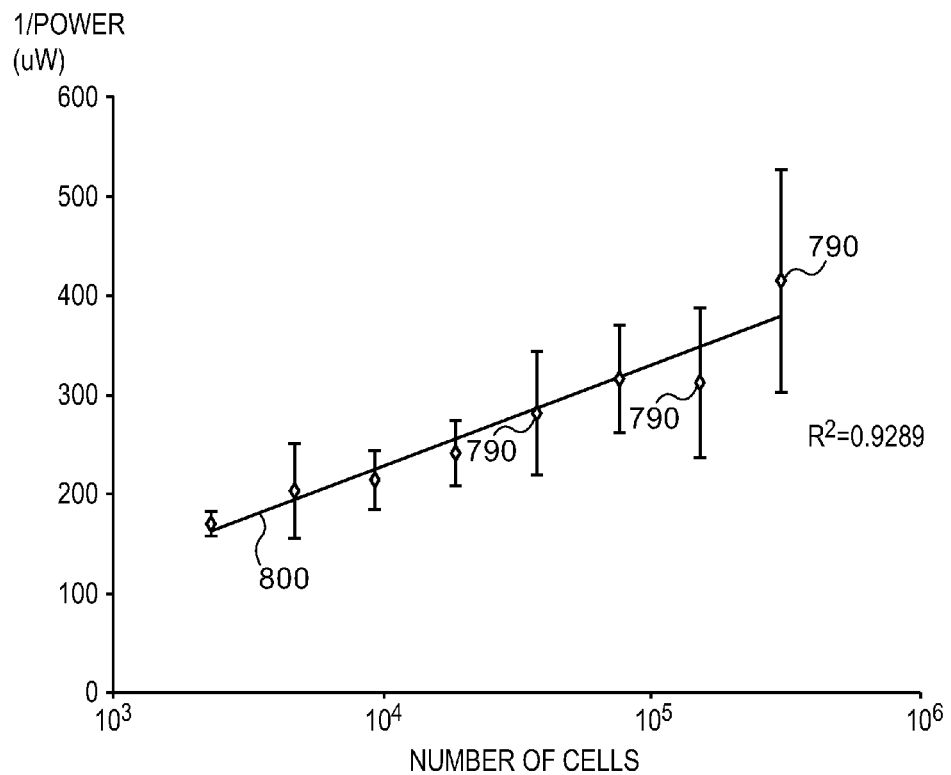
FIG. 15 illustrates a graph of the absorption response of light within cancerous cells.

FIG. 15 shows a graph of the absorption response of output power vs. number of cancerous cells, i.e. the amount of absorption of light within tissue as a function of the number of cancerous cells within the tissue, where the x-axis represents the number of cancerous cells within the tissue and the y-axis represents the absorption amount in microwatts. In particular, the graph illustrates the absorption response within a human cancer cell line provided by American Type Culture Collection (ATCC) of Manassas, Va., with ATCC number CRL-1435 and a PC-3 designation.

A plurality of absorption responses 790 are illustrated along with the standard deviation of each absorption response. As shown by linear line 800, which represents an average of the plurality of absorption responses 790, as the number of cancerous cells increase the light absorption within the tissue generally increases. Thus, the intensity of the light reflected off of the target area can be detected and the ratio between the intensity of the reflected light and the output light will be indicative of the number of cancerous cells within the tissue. In particular, light sensor array 40 of FIG. 3 detects narrow band light 31 after interaction with the target area. The control circuitry compares the intensity of narrow band light 31 after interaction with the target area with the intensity of narrow band light 31 before interaction with the target area, i.e. when output by narrow band light source 30. In the event that the difference between the compared intensities is greater than a predetermined absorption threshold, a tissue information signal is output indicative that unhealthy tissue is present within the target area. In another embodiment, a separate narrow band light, exhibiting a different wavelength is utilized. FIG. 15 additionally indicates the accuracy of average 800, denoted $R^2$. In the illustrated graph of FIG. 15 $R^2$ indicates an accuracy of 92.89%.

Figure 16:
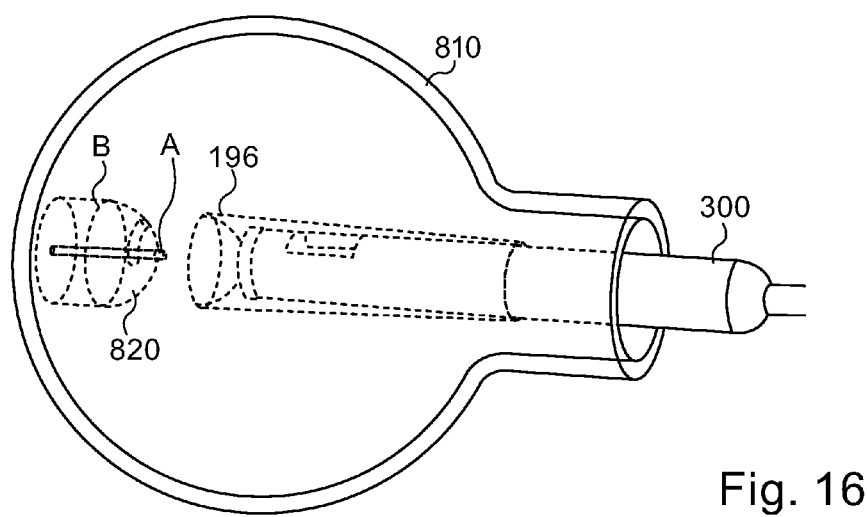
FIG. 16 illustrates a searching profile of the probe of FIGS. 11A-11C within the vagina.

FIG. 16 schematically illustrates a searching profile of probe 300 of FIGS. 11-12 within a vagina 810. Probe 300 is inserted into vagina 810 and attached to cervix 820. As illustrated, probe 300 comprises a cervix attachment member 196. The shape of cervix attachment member 196 is designed to efficiently mate with the shape of the cervix. As described above in relation to FIGS. 11B-11C, probe 300 comprises a plurality of motors arranged to translate the optical units in a plurality of directions. In one embodiment, scanning of cervix 820 begins at the cervix opening, denoted point A. Probe 300 is arranged to scan the entire face of cervix 820 until reaching the border of the scannable area of cervix 820, denoted border B. In one embodiment, the scanning is performed in a spiral configuration and in another embodiment the scanning is performed in a linear configuration. In another embodiment, cervix 820 may be scanned in a dedicated pattern in order to concentrate on a specific area of cervix 820.

Figure 17:
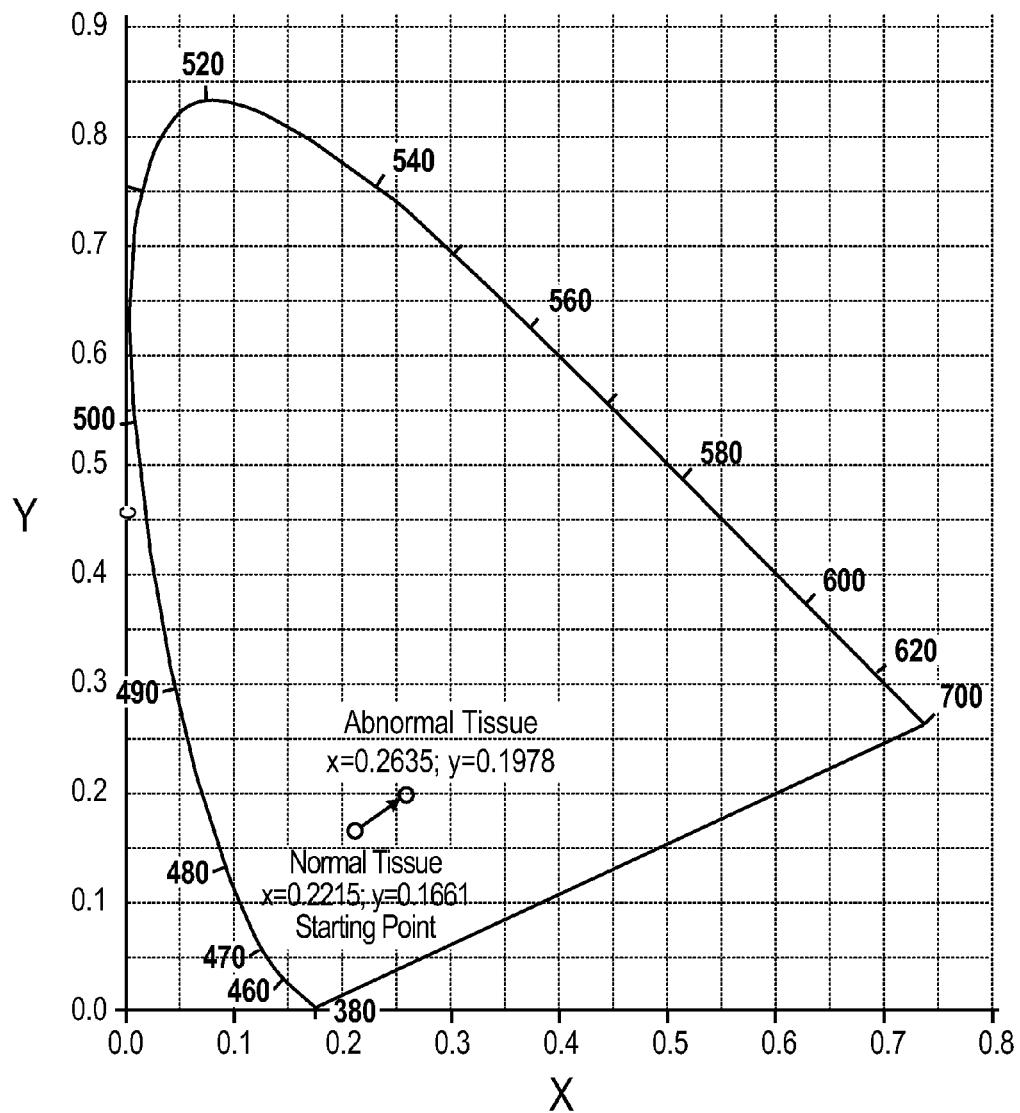
FIG. 17 illustrates the chromatic impact of interaction of broad band light with unhealthy tissue versus healthy tissue, in relation to the CIE 1931 color space.

FIG. 17 illustrates the chromatic impact of the interaction of broad band light with unhealthy tissue versus healthy tissue, in relation to the CIE 1931 color space. As illustrated, a broad band light reflected off a cervical surface containing healthy tissue exhibits a first set of color space coordinates and broad band light reflected off a cervical surface containing unhealthy tissue exhibits a second set of color space coordinates, different than the first set of color space coordinates.

Figure 18:
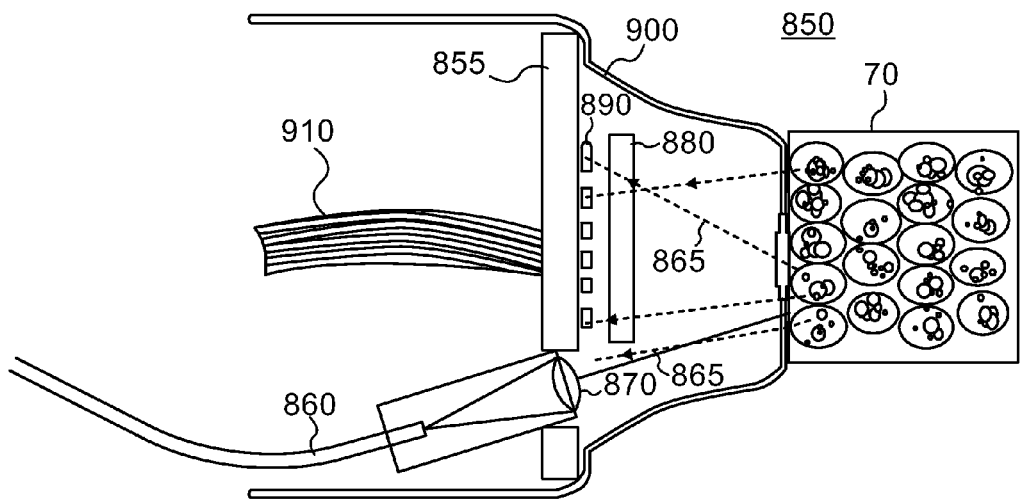
FIG. 18 illustrates a high level schematic diagram of a chromatic impact determination unit, according to certain embodiments.

FIG. 18 illustrates a high level schematic diagram of a chromatic impact determination unit 850 arranged to determine the change in the chromatic impact of broad band light after interaction with a target area 70 of a cervix. Chromatic impact determination unit 850 comprises: a printed circuit board (PCB) 855; a broad band light source 860, illustrated as an optical fiber; a collimating lens 870; a colorimetric filter 880; a color sensor array 890; a cover 900; and a data cable 910. Broad band light source 860 is arranged to output a broad band light, preferably a white light, and is in optical communication with collimating lens 870. Color sensor array 890 is implemented on PCB 855 and is in optical communication with colorimetric filter 880. Optionally, color sensor array 890 may be replaced with a single color sensor without exceeding the scope. Data cable 910 is in communication with an external computing system (not shown) arranged to process the information received from color sensor array 890 via data cable 910. In one embodiment, broad band light source 860 comprises a white LED.

In operation, as described above in relation to imaging unit 100 of FIG. 4, broad band light source 860 outputs a broad band light 865, preferably a white light. The output broad band light 865 is focused by collimating lens 870 to irradiate target area 70 through cover 900. The broad band light 865 reflected off of target area 70 is filtered by colorimetric filter 880 and received by color sensor array 890. Color sensor array 890 is in one embodiment arranged to determine the coordinates on the CIE 1931 color space of the received broad band light 865, however this is not meant to be limiting in any way and color sensor array, optionally in cooperation with a control circuitry, is arranged to determine the chromatic result of the received broad band light 865 in any of a plurality of methods known to the prior art. The determined color coordinates of the received broad band light 865 are compared with the color coordinates of the broad band light 865 when output from broad band light source 860. In the event that the difference between the color coordinates of broad band light 865 when output from broad band light source 860 and broad band light 865 after interaction with target area 70 is greater than a predetermined chromatic impact shift value, the control circuitry outputs a tissue information signal indicative that target area 70 exhibits unhealthy tissue. In one embodiment, the magnitude of the vector between the color coordinates of broad band light 865 when output from broad band light source 860 and broad band light 865 after interaction with target area 70 is compared to the predetermined chromatic impact shift value. In another embodiment, the chromaticity of the received broad band light 865 is compared to a known chromaticity of broad band light after interaction with healthy tissue and in the event the difference is greater than a predetermined value the control circuitry outputs a tissue information signal indicative that target area 70 exhibits unhealthy tissue.

Figure 19:
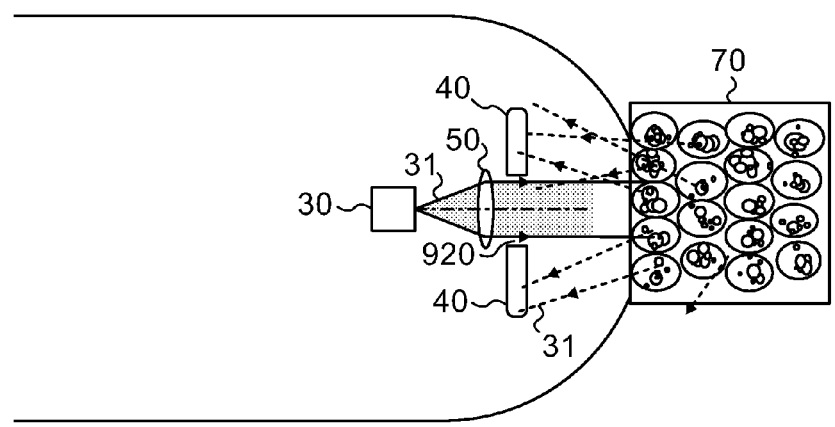
FIG. 19 illustrates a high level schematic diagram of various elements of the light scattering determination unit comprising a light sensor array exhibiting an opening for light, according to certain embodiments.

FIG. 19 illustrates a high level schematic diagram of various elements of light scattering determination unit 10, where the output narrow band light 31 is arranged to pass through an opening 920 in light sensor array 40. In particular, light sensor array 40 is constructed and positioned to exhibit an opening 920 large enough to pass narrow band light 31 there through. Collimating lens 50 is positioned so that narrow band light 31 output by narrow band light source 30 is focused by collimating lens 50 to irradiate target area 70 through opening 920 of light sensor array 40. Opening 920 is described as being related to a light sensor array 40, however this is not meant to be limiting in any way and an opening 920 can be present in any of the light sensors described above, particularly a CCD or CMOS sensor.

FIGS. 20A-20B illustrate a high level schematic diagram of a face of light sensor array 40 exhibiting opening 920. As shown in FIG. 20B, narrow band light 31 passes through opening 920 and is reflected off of the target area to be received by light sensor array 40.

Thus, the above embodiments provide for a single probe arranged to provide for detection of unhealthy tissue. In particular, as described above, 4 separate tests are provided in the single probe for detection of unhealthy tissue:

1. Determination of the spatial scattering of a narrow band light after interaction with a target area of an organ. As described above in relation to FIG. 3, the narrow band light is optionally a monochromatic coherent light, such as a laser. The spatial scattering is determined responsive to the pattern of the light received by a light sensor after interaction with the target area. In the event that the spatial scattering is greater than a predetermined scattering threshold, a tissue information signal is output indicating that unhealthy tissue is present within the target area.

2. Identification of an abnormality in an image output by a light sensor responsive to receiving a broad band light after interaction with the target area. In one embodiment, as described above in relation to FIG. 4 a ratio between the number of pixels exhibiting an intensity greater than an average intensity and the number of pixels exhibiting an intensity less than the average intensity. In the event that the ratio is greater than a predetermined intensity ratio threshold, a tissue information signal is output indicating that unhealthy tissue is present within the target area. In another embodiment, as described above in relation to FIGS. 13A-14, a Fourier transform of the means in the vertical direction of the image is determined. In the event the ratio between the high frequencies and the low frequencies of the Fourier transform is greater than a predetermined frequency ratio threshold, a tissue information signal is output indicating that unhealthy tissue is present within the target area. As described above, in one embodiment a single light sensor is used for tests 1 and 2.

3. Determination of the chromatic impact of interaction of a broad band light with the target area. As described above in relation to FIG. 18, the broad band light is detected by a color sensor. In one embodiment the broad band light is a white light. Optionally, a separate broad band light is not provided and the color sensor is arranged to detect the broad band light of the image abnormality test. In one embodiment, the difference between the color coordinates of the broad band light after interaction with the target area and before interaction with the target area is determined. In the event that the determined difference is greater than a predetermined chromatic impact shift value, a tissue information signal is output indicative that unhealthy tissue is present within the target area. In another embodiment, the difference between the color coordinates of the received broad band light and the know color coordinates of broad band light after interaction with healthy tissue is determined. In the event that the determined difference is greater than a predetermined value, a tissue information signal is output indicative that unhealthy tissue is present within the target area.

4. Determination of the amount of absorption of a narrow band light within the target area. As described above in relation to FIG. 15, the narrow band light is detected by a light sensor. In one embodiment, a separate narrow band light is not provided and the absorption test is performed on the narrow band light received by the light sensor of the spatial scattering test. The intensity of the narrow band light after interaction with the target area is compared to the intensity of the narrow band light before interaction with the target area. In the event that the difference between the compared intensities is greater than a predetermined absorption threshold, a tissue information signal is output indicative that unhealthy tissue is present within the target area. It is to be noted that the spatial scattering properties of the tissue affect the intensity of light received by the light sensor and the absorption properties of the tissue affect the scattering of the light. Therefore, in order to improve the spatial scattering test and the light absorption test, in one embodiment separate narrow band lights, exhibiting different wavelengths are utilized. For the spatial scattering test a laser exhibiting a wavelength of 950 nm is utilized and for the light absorption test a laser exhibiting a wavelength of 810 nm is utilized.

The combination of the above tests provide for accurate diagnosis of tissue disease. In particular, a narrow band light is able to penetrate to a greater depth than a broad band light. For example, a white light is able to penetrate 0.5 mm of tissue and a laser is able to penetrate 5 mm of tissue. Thus, the combination of the broad band light and narrow band light tests provide diagnosis in multiple depths of the target area.

Group B Streptococcal Disease Detection Probe

Group B *Streptococcus* (GBS), also known as '*Streptococcus agalactiae*', is a genus of spherical gram-positive *streptococcus*. It is part of the normal flora of the intestines and genital tract and is found in 20-40% of women. GBS is a human pathogen that causes significant medical problems during pregnancy and in neonates. GBS strains are subclassified into nine serotypes according to the immunologic reactivity of the polysaccharide capsule. Serotype III is responsible for 80% of neonatal meningitis.

Figure 21B:
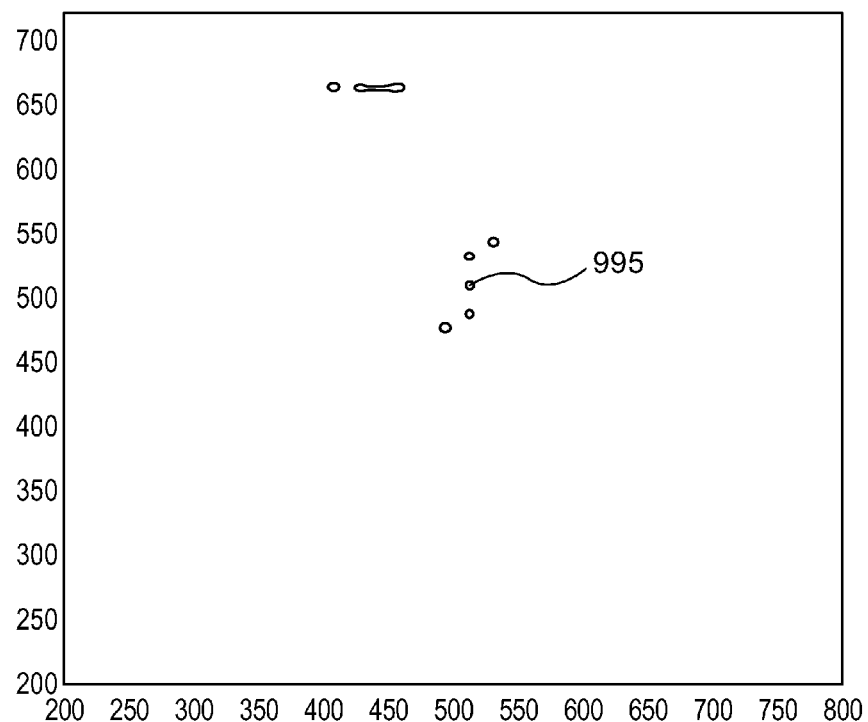
FIG. 21B illustrates the image of FIG. 21A after application of a GBS detection algorithm, according to certain embodiments.
Figure 22:
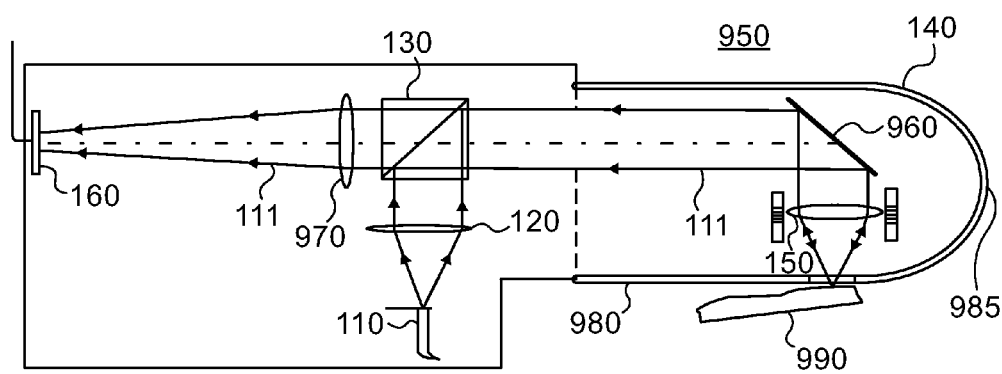
FIG. 22 illustrates a probe arranged to detect GBS.

FIG. 21A illustrates an image of a GBS strain 940; FIG. 21B illustrates the image of FIG. 21A after application of a GBS detection algorithm as will be described below; and FIG. 22 illustrates a probe 950 arranged to detect GBS, the figures being described together. Probe 950 is in all respects similar to imaging unit 100 of FIG. 4, with the exception that a mirror 960 is provided in optical communication with beam splitter 130 and objective lens 150 and is arranged to reflect broad band light 111 from beam splitter 130 to objective lens 150, objective lens 150 positioned such that broad band light 111 exits cover 140 from a side 980 of cover 140 and not through the front 985 of cover 140 which leads probe 950 into the vagina. Additionally, a light sensor objective lens 970 is provided in optical communication with beam splitter 130 and light sensor 160 and is arranged to reflect broad band light 111 from beam splitter 130 to light sensor 160.

In operation, as described above in relation to imaging unit 100, a broad band light 111 is output by broad band light source 110. Output broad band light 111 passes through astigmatic element 120. Broad band light 111 is then reflected by beam splitter 130 to mirror 960 and focused by objective lens 150 to irradiate a target area 990 of a birth canal or anal sphincter. Broad band light 111 is reflected off of target area 990, through objective lens 150 and is reflected off of mirror 960 to beam splitter 130. Broad band light 111 is passed to light sensor objective lens 970 which focuses broad band light 111 onto light sensor 160.

Light sensor 160 is arranged to output an image of target area 990 to a control circuitry (not shown) which is arranged to determine if GBS is present within target area 990. In particular, a correlation function is determined between the received image of target area 990 and an image of a single GBS bacterium. FIG. 21B illustrates an image of "bright spots" 995 in the correlation function, i.e. sections of the image where a correlation is found with a single GBS bacterium. In the event that at least a predetermined number of "bright spots" 995 are detected exhibiting a distance between each other which corresponds to the distance between single GBS bacteria in a GBS strain, the control circuitry is arranged to output a correlation signal indicative that GBS is present within target area 990. In one non-limiting embodiment, the predetermined number of "bright spots" 995 is 5. As described above in relation to probe 300, in one embodiment probe 950 is further arranged to scan the entire birth canal and/or anal sphincter to determine if GBS is present.

Advantageously, probe 950 allows for rapid identification of GBS which can improve prevention of GBS infection of babies during birth, thereby overcoming some of the inherent limitations in late antenatal screening.

When a patient exhibiting signs of labor (regular contractions, rupture of membrane or vaginal bleeding) arrives at the delivery room, the Obstetrician can use probe 950 to determine if GBS is present in the birth canal and/or anal sphincter. Preferably, light sensor 160 is able to provide an image with a resolution of 1 µm. For comparison, cell size is about 30 µm and the size of GBS bacterium is approximately 10 µm. Probe 950 thus provides a simple bedside procedure to detect GBS having a turn-around time of less than a minute and exhibiting sensitivity and specificity greater than 95%. This allows to minimize the use of antibiotic treatment during and after birth.

Figure 23A:
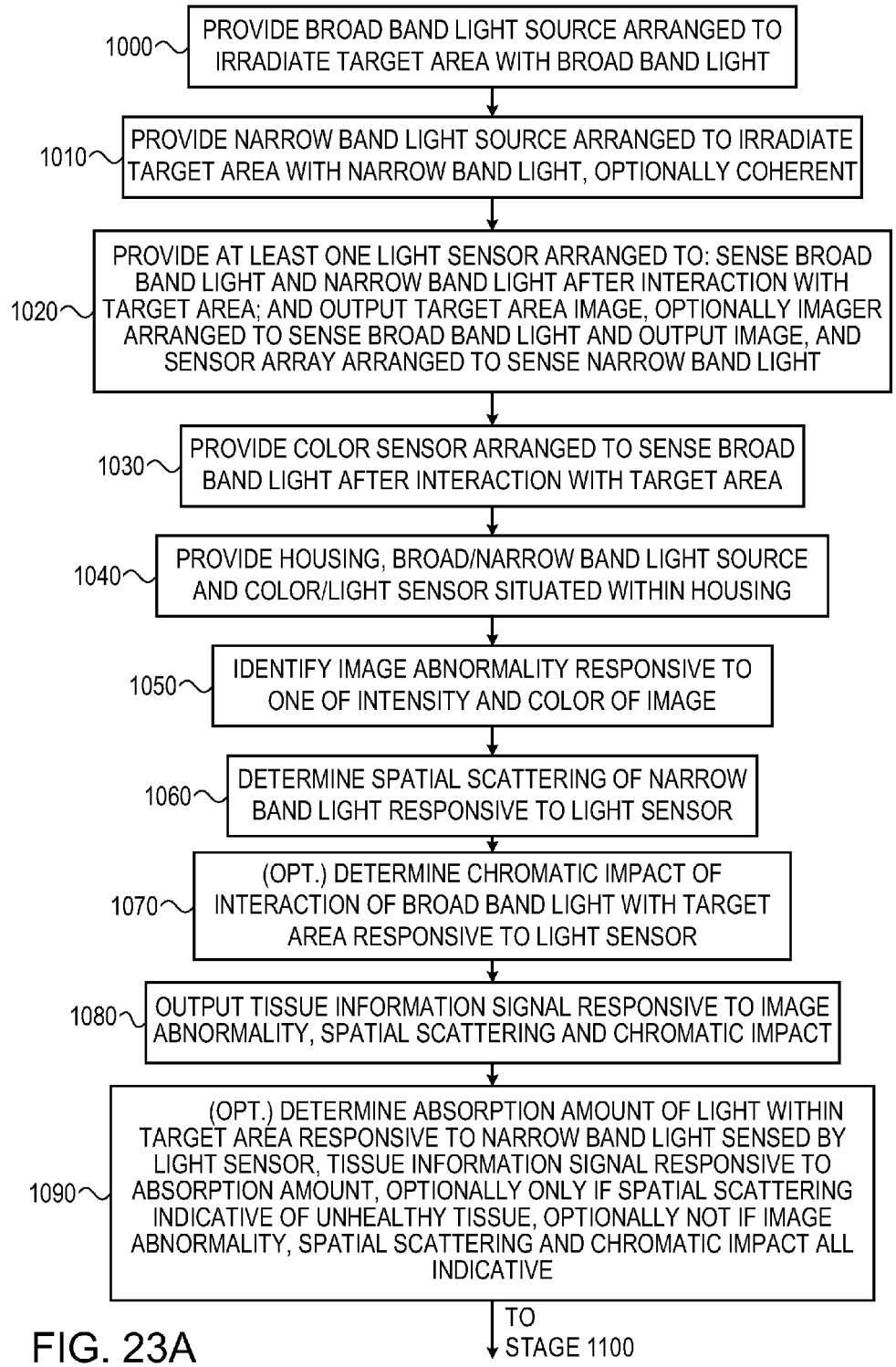
FIGS. 23A-23B illustrate a high level flow chart of a method of tissue disease diagnosis, according to certain embodiments.
Figure 23B:
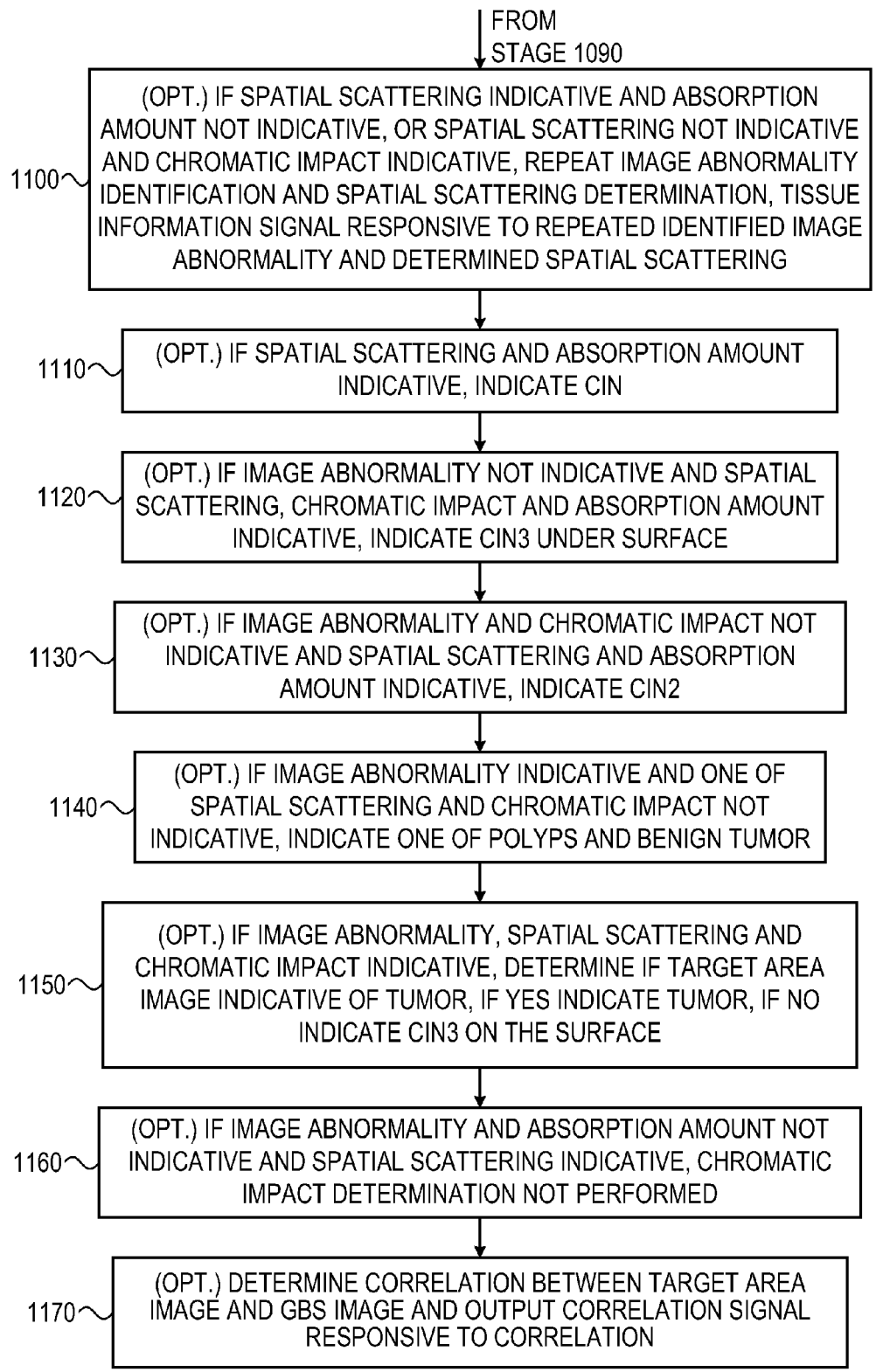

FIGS. 23A-23B illustrate a high level flow chart of a method of tissue disease diagnosis, according to certain embodiments, the figures being described together. In stage 1000, a broad band light source is provided arranged to irradiate a target area of an organ, optionally a cervix, with a broad band light. As described above, in one embodiment the broad band light source is a white LED. In stage 1010, a narrow band light source is provided arranged to irradiate the target area of the organ with a narrow band light. Optionally, the narrow band light is a narrow band coherent light, further optionally a laser.

In stage 1020, at least one light sensor is provided arranged to: sense the broad band light of stage 1000 after interaction with the target area; and sense the narrow band light of stage 1010 after interaction with the target area. The at least one light sensor is further arranged to output an image of the target area responsive to the received broad band light. Optionally, the at least one light sensor comprises: an imager, such as a CCD or CMOS imager; and a light sensor array, such as a PIN sensor array or an APD sensor array. The imager is arranged to sense the broad band light of stage 1000 after interaction with the target area and the light sensor array is arranged to sense the narrow band light of stage 1010 after interaction with the target area.

In stage 1030, a color sensor is provided arranged to sense the broad band light of stage 1000 after interaction with the target area. In stage 1040, a housing is provided. The broad band light source of stage 1000, the narrow band light source of stage 1010, the at least one light sensor of stage 1020 and the color sensor of stage 1030 are all situated within the provided housing.

In stage 1050, the image of stage 1020 is examined to identify an image abnormality responsive to one of the intensity and color of the image, as described above in relation to imaging unit 100 of FIG. 4 and in relation to the method described in FIGS. 13A-14. In one embodiment, the image abnormality is a disuniformity in the image. In one embodiment, the image is a raster image and the image abnormality is identified responsive to one of the intensity and color of the pixels of the image. In stage 1060, the spatial scattering of the narrow band light of stage 1010 after interaction with the target area is determined, responsive to the receiving of the narrow band light by the light sensor of stage 1020, as described above in relation to spatial scattering determination unit 10 of FIG. 3. In optional stage 1070, the chromatic impact of the interaction of the broad band light of stage 1000 with the target area is determined, responsive to the receiving of the broad band light by the light sensor of stage 1020, as described above in relation to chromatic impact determination unit 850 of FIG. 18.

In stage 1080, a tissue information signal is output responsive to the image abnormality identification of stage 1050, the determined spatial scattering of stage 1060 and the determined chromatic impact of optional stage 1070, the output tissue information signal indicative of the diagnosis status of the tissue within the target area. In optional stage 1090, the amount of absorption of narrow band light within the target area is determined responsive to the narrow band light of stage 1010 being sensed by the at least one light sensor of stage 1020 after interaction with the target area. As described above in relation to FIG. 15, the intensity of the narrow band light after interaction with the target area is determined and compared with the intensity of the narrow band light before interaction with the target area. The output tissue information signal of stage 1080 is further responsive to the determined narrow band light absorption amount. Optionally, the absorption amount is determined only in the event that the determined spatial scattering of stage 1060 is indicative that the tissue within the target area is unhealthy. Optionally, in the event that the image abnormality identification of stage 1050, the determined spatial scattering of stage 1060 and the determined chromatic impact of optional stage 1070 are each indicative of unhealthy tissue within the target area, the absorption amount is not determined. Advantageously, it is not necessary to determine the absorption amount since in such a case the absorption amount test will not add any information about the diagnosis status of the tissue.

In optional stage 1100, in the event that the determined spatial scattering of stage 1060 is indicative of unhealthy tissue within the target area and the determined absorption amount of optional stage 1090 is not indicative of unhealthy tissue within the target area, the image abnormality identification of stage 1050 and the spatial scattering determination of stage 1060 are repeated. The repetition is performed since the spatial scattering test and the absorption amount test have given conflicting diagnoses and thus there is a possibility that CIN3 is present within the tissue of the target area, however it is not confirmed. Optionally, the chromatic impact determination of optional stage 1070 and/or the absorption amount determination of optional stage 1090 are also determined. The output tissue information signal of stage 1080 is further responsive to the repeated image abnormality identification and spatial scattering determination. Optionally, the output tissue information signal is additionally responsive to the optionally repeated chromatic impact determination and/or the optionally repeated absorption amount determination. Additionally, in the event that the determined spatial scattering of stage 1060 is not indicative of unhealthy tissue within the target tissue and the determined chromatic impact of optional stage 1070 is indicative of unhealthy tissue within the target tissue, the image abnormality determination of stage 1050 and the spatial scattering determination of stage 1060 are repeated. Optionally, the chromatic impact determination of optional stage 1070 and/or the absorption amount determination of optional stage 1090 are also determined.

In optional stage 1110, in the event that both the determined spatial scattering of stage 1060 and the determined absorption amount of optional stage 1090 are indicative of unhealthy tissue within the target area, the output tissue information signal of stages 1080-1090 comprises an indication that CIN is present within the tissue of the target area. In particular, either CIN2 or CIN3 is present, as will be described below.

In optional stage 1120, in the event that: the image abnormality identification of stage 1050 is not indicative of unhealthy tissue within the target area; and the determined spatial scattering of stage 1060, the determined chromatic impact of optional stage 1070 and the determined absorption amount of optional stage 1090 are each indicative of unhealthy tissue within the target area, the output tissue information signal of stage 1080-1090 is arranged to comprises an indication that CIN3 is present in tissue under the surface of the target area.

In optional stage 1130, in the event that: the image abnormality identification of stage 1050 and the determined chromatic impact of optional stage 1070 are each not indicative of unhealthy tissue within the target area; and the determined spatial scattering of stage 1060 and the determined absorption amount of optional stage 1090 are each indicative of unhealthy tissue within the target area, the output tissue information signal of stages 1080-1090 is arranged to comprises an indication that CIN2 is present in the tissue within the target area.

In optional stage 1140, in the event that: the image abnormality identification of stage 1050 is indicative of unhealthy tissue within the target area; and at least one of the determined spatial scattering of stage 1060 and the determined chromatic impact of optional stage 1070 is not indicative of unhealthy tissue within the target area, the output tissue signal of stage 1080 is arranged to comprise an indication that one of cervical polyps and a benign tumor is present within the target area.

In optional stage 1150, in the event that each of the image abnormality identification of stage 1050, the determined spatial scattering of stage 1060 and the determined chromatic impact of optional stage 1070 is indicative of unhealthy tissue within the target area, the information received by the at least one light sensor of stage 1020 regarding the received broad band light after interaction with the target area is examined to determine if it is indicative of a tumor within the target area. In one embodiment, the at least one light sensor comprises a CCD or CMOS imager, the imager providing an image of the target area responsive to the received broad band light. Contours of the target area image are examined to determine if a tumor is present in the target area. In the event that the image is indicative of a tumor within the target area, the output tissue information signal of stage 1080 is arranged to comprise an indication that a tumor is present within the target area. In the event that the image is not indicative of a tumor within the target area, the output tissue information signal of stage 1080 is arranged to comprise an indication that CIN3 is present within tissue on the surface of the target area.

In optional stage 1160, in the event that the image abnormality identification of stage 1050 and the determined absorption amount of optional stage 1090 are not indicative of unhealthy tissue within the target area, the chromatic impact determination of optional stage 1070 is not performed.

In optional stage 1170, the at least one light sensor of stage 1020 comprises an imager, the imager arranged to provide an image of the target area. In one embodiment, the target area is a target area of a birth canal or anal sphincter. The target area image is compared with an image of a single GBS bacterium and a correlation function is determined between the target area image and the GBS image, as described above in relation to FIGS. 21A-22. A correlation signal is output responsive to the determined correlation, as described above, to indicate if GBS is present within the target area.

Stages 1000-1170 have been described above in a sequential order however this is not meant to be limiting in any way and the order of the stages may differ, without exceeding the scope.

Table 2 shows a plurality of states of a control circuitry arranged to control the above described device of stages 1000-1160. The term "positive" as used in table 2 is defined as meaning that the particular test is indicative of unhealthy tissue within the target area and the term "negative" as used in table 2 is defined as meaning that the particular test is not indicative of unhealthy tissue within the target area. The term "don't care" as used in table 2 is defined as meaning that the particular test is irrelevant to the diagnosis of the tissue of the target area. The term "repeat tests" as used in table 2 is defined as meaning that the tests of stages 1050-1060 and optionally the tests of stages 1070 and 1090 need to be repeated, as described above in relation to optional stage 1100.

TABLE 2

| Image abnormality | Spatial Scattering | Chromatic impact | Absorption Amount | Diagnosis |
|---|---|---|---|---|
| Negative | Negative | Negative | Don't Care | Tissue healthy |
| Negative | Positive | Don't Care | Negative | Repeat Tests |
| Negative | Negative | Positive | Negative | Repeat Tests |
| Negative | Negative | Negative | Positive | Repeat Tests |
| Negative | Negative | Positive | Positive | Repeat Tests |
| Negative | Positive | Positive | Positive | CIN3 Under Surface |
| Negative | Positive | Negative | Positive | CIN2 |
| Positive | Negative | Negative | Don't Care | Polyps or Benign Tumor |
| Positive | Positive | Negative | Negative | Polyps or Benign Tumor & Repeat Tests |
| Positive | Positive | Positive | Don't Care | CIN3 on Surface or Tumor |
| Positive | Positive | Negative | Positive | Polyps or Benign Tumor & CIN2 |
| Positive | Negative | Positive | Don't Care | Polyps or Benign Tumor & Repeat Tests |

Figure 24A:
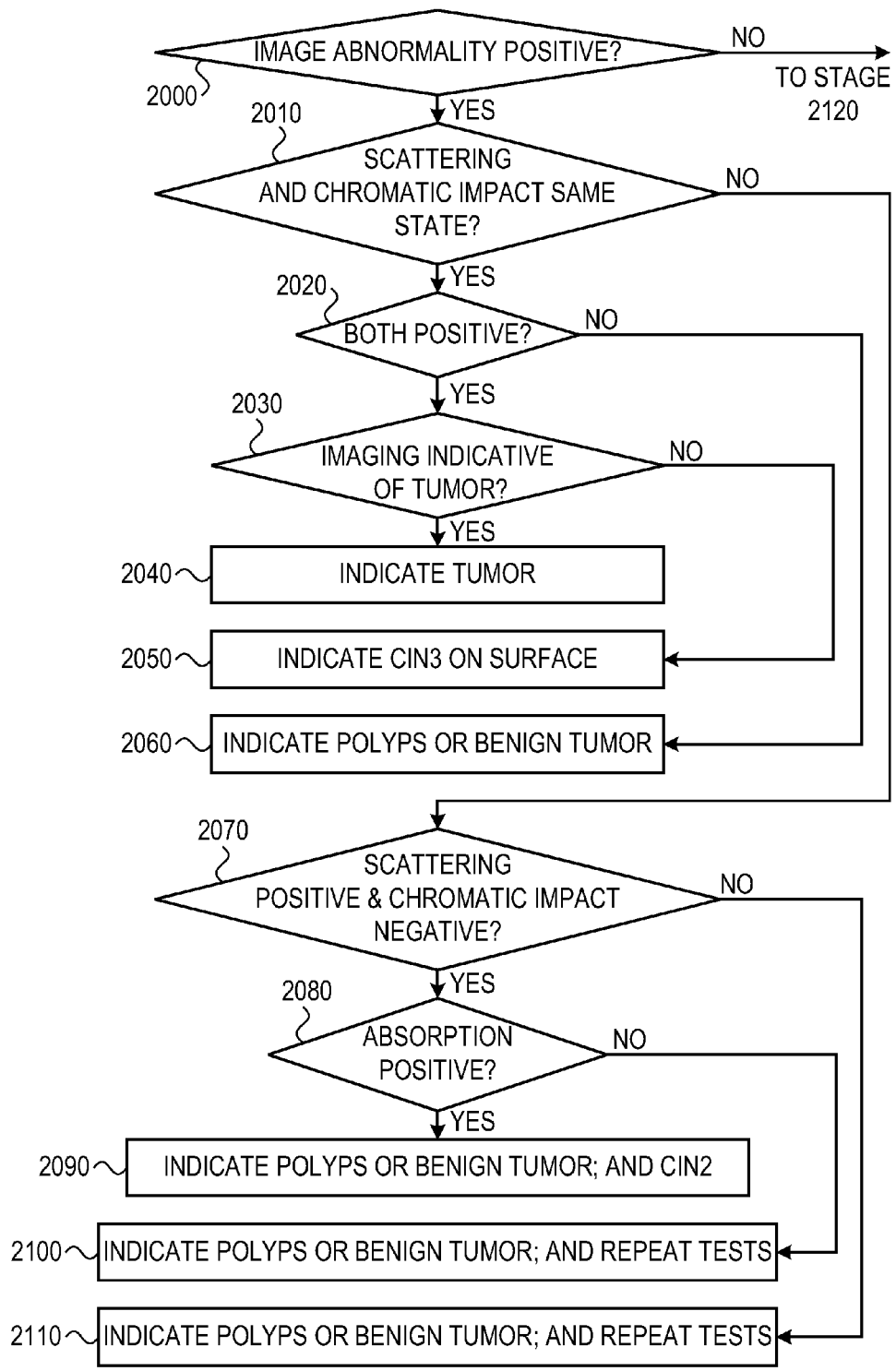
FIGS. 24A-24B illustrate a high level flow chart of the steps of a control circuitry for diagnosing tissue disease, according to certain embodiments.
Figure 24B:
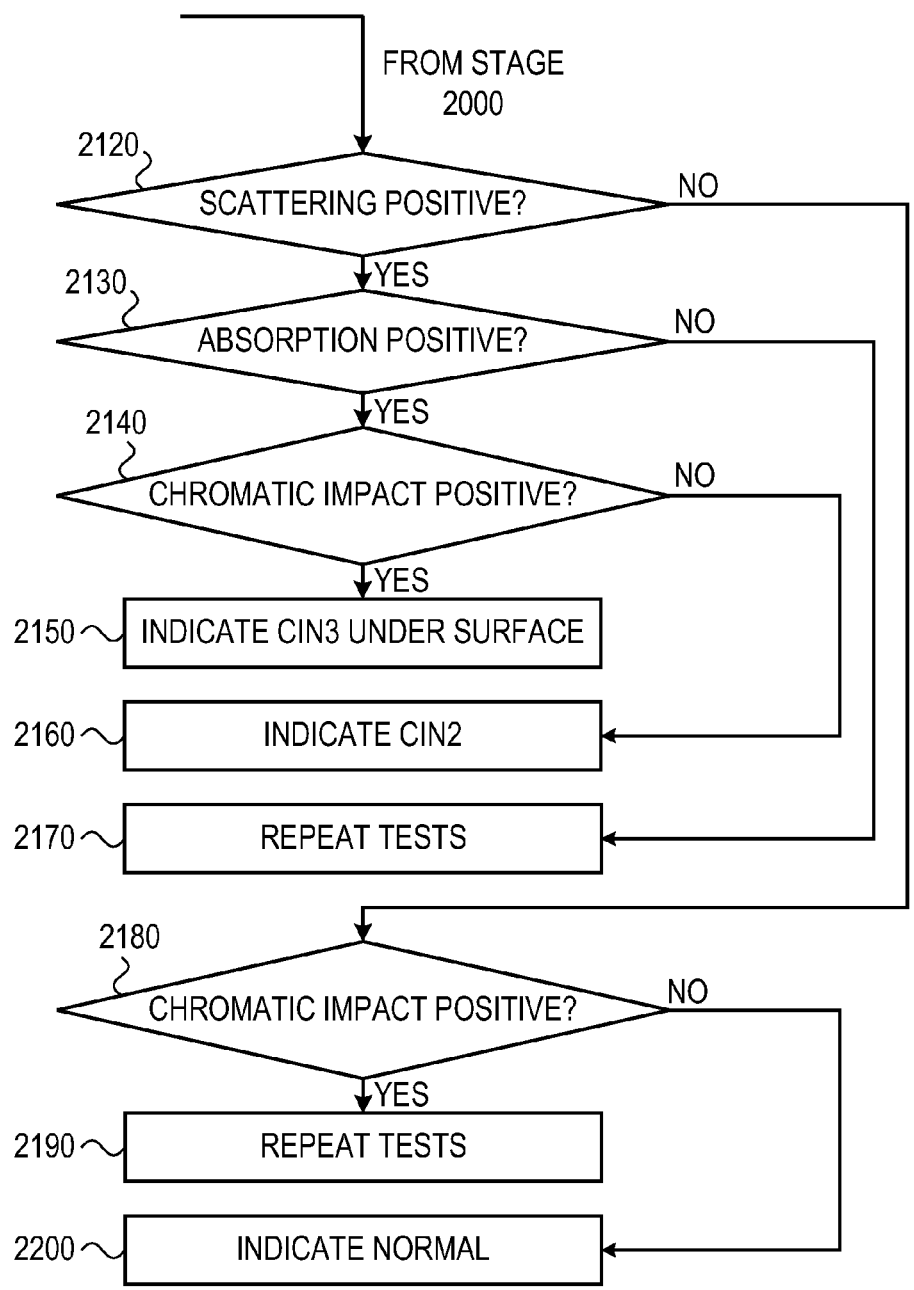

In one embodiment, a control circuitry is arranged to perform the above tests in a sequence described in the flow chart of FIGS. 24A-24B. The terms "positive", "negative" and "repeat tests" are defined above in relation to table 2. In stage 2000, an image is examined to identify an image abnormality responsive to one of intensity and color of the image, optionally intensity and color of pixels of the image, as described above in relation to stage 1050. As described above in relation to imaging unit 100 of FIG. 4 and the method of FIGS. 13A-14, an image abnormality is indicative that unhealthy tissue is present in the target area. In the event that the image abnormality identification is positive, in stage 2010 the spatial scattering is determined, as described above in relation to stage 1060, and the chromatic impact is determined, as described above in relation to optional stage 1070. As described above in relation to light scattering determination unit 10 of FIG. 3, the determined spatial scattering is examined to determine if unhealthy tissue is present within the target area. Additionally, as described above in relation to chromatic impact determination unit 850 of FIG. 18, the determined chromatic impact is examined to determine if unhealthy tissue is present within the target area.

In the event that both the determined spatial scattering and chromatic impact are of the same state, i.e. both positive or both negative, in stage 2020 the control circuitry is arranged to determine if both the determined spatial scattering and chromatic impact are positive. In the event that both the determined spatial scattering and chromatic impact are positive, in stage 2030 the control circuitry is arranged to examine an image of the target area to determine if a cancerous tumor is present within the target area, as described above in relation to optional stage 1150. In the event that the image of the target area is indicative of a cancerous tumor, in stage 2040 a tissue information signal is output indicating that a cancerous tumor is present within the target area. In the event that in stage 2030 the image of the target area is not indicative of a cancerous tumor, in stage 2050 a tissue information signal is output indicating that CIN3 is present on the surface of the target area.

In the event that in stage 2020 the control circuitry determines that both the determined spatial scattering and chromatic impact are negative, in stage 2060 a tissue information signal is output indicating that cervical polyps of a benign tumor is present within the target area. In the event that in stage 2010 the control circuitry determines that the determined spatial scattering and chromatic impact are not of the same state, in stage 2070 the control circuitry is arranged to determine if the determined spatial scattering is positive and the determined chromatic impact is negative.

In the event that the determined spatial scattering is positive and the determined chromatic impact is negative, in stage 2080 the light absorption amount of the target area is determined, as described above in relation to optional stage 1090. As described above in relation to FIG. 15, the determined light absorption amount is examined to determine if unhealthy tissue is present within the target area. In the event that the determined light absorption amount is positive, in stage 2090 a tissue information signal is output indicating that either cervical polyps or a benign tumor is present within the target area. Additionally, the output signal indicates that CIN2 is present within the target tissue.

In the event that in stage 2080 the determined light absorption amount is negative, in stage 2100 a tissue information signal is output indicating that either cervical polyps or a benign tumor is present within the target area. Additionally, the output tissue information signal indicates that at least one of the test results are faulty and stage 2000, as described above, is repeated. In one embodiment, the output tissue information signal is not indicative of the faulty test result, however stage 2000 is repeated. In the event that in stage 2070 the determined spatial scattering is negative and the determined chromatic impact is positive, in stage 2110 a tissue information signal is output indicating that either cervical polyps or a benign tumor is present within the target area. Additionally, the output tissue information signal indicates that at least one of the test results are faulty and stage 2000, as described above, is repeated. In one embodiment, the output tissue information signal is not indicative of the faulty test result, however stage 2000 is repeated. In the event that in stage 2000, described above, the image abnormality identification is negative, in stage 2120 the spatial scattering is determined, as described above in relation to stage 1060. As described above in relation to light scattering determination unit 10 of FIG. 3, the determined spatial scattering is examined to determine if unhealthy tissue is present within the target area. In the event that the determined spatial scattering is positive, in stage 2130 the control circuitry is arranged to determine the light absorption amount of the target area is determined, as described above in relation to optional stage 1090. As described above in relation to FIG. 15, the determined light absorption amount is examined to determine if unhealthy tissue is present within the target area. In the event that the determined light absorption amount is positive, in stage 2140 the control circuitry is arranged to determine the chromatic impact, as described above in relation to optional stage 1070. As described above in relation to chromatic impact determination unit 850 of FIG. 18, the determined chromatic impact is examined to determine if unhealthy tissue is present within the target area.

In the event that the chromatic impact is positive, in stage 2150 a tissue information signal is output indicating that CIN3 is present under the surface of the target area. In the event that in stage 2140 the determined chromatic impact is negative, in stage 2160 a tissue information signal is output indicating the CIN2 is present within the target area. In the event that in stage 2130 the determined absorption amount is negative, in stage 2170 a tissue information signal is output indicating that at least one of the test results are faulty and stage 2000, as described above, is repeated. In one embodiment, the output tissue information signal is not indicative of the faulty test result, however stage 2000 is repeated.

In the event that in stage 2120 the determined spatial scattering is negative, in stage 2180 the control circuitry is arranged to determine the chromatic impact as described above in relation to optional stage 1070. As described above in relation to chromatic impact determination unit 850 of FIG. 18, the determined chromatic impact is examined to determine if unhealthy tissue is present within the target area. In the event that the determined chromatic impact is positive, in stage 2190 a tissue information signal is output indicating that at least one of the test results are faulty and stage 2000, as described above, is repeated. In one embodiment, the output tissue information signal is not indicative of the faulty test result, however stage 2000 is repeated. In the event that in stage 2180 the determined chromatic impact is negative, in stage 2200 a tissue information signal is output indicating that the tissue within the target area is normal and healthy.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. A tissue disease diagnosis apparatus, the apparatus comprising:
   control circuitry;
   a broad band light source configured to output broad band light and irradiate a target area of an organ with said output broad band light;
   a narrow band light source configured to output narrow band light and irradiate the target area of the organ with said output narrow band light;
   at least one light sensor in communication with said control circuitry, said at least one light sensor configured to:
   sense said broad band light after interaction with the target area and output an image of the target area responsive to said sensed broad band light, and
   sense said narrow band light after interaction with the target area and outputs a signal responsive to said sensed narrow band light;
   a color sensor in communication with said control circuitry and configured to sense said broad band light after interaction with the target area and outputs a signal responsive to said sensed broad band light; and
a housing, said broad band light source, narrow band light source, at least one light sensor and color sensor situated within said housing,
wherein said control circuitry is configured to:
identify an abnormality in the image output by said at least one light sensor, the abnormality identification responsive to one of the intensity and color of the image;
determine spatial scattering of said sensed narrow band light responsive to the output signal of said at least one light sensor;
determine chromatic impact of the interaction of said output broadband light with the target area, responsive to the output signal of said color sensor; and
output a tissue information signal responsive to said image abnormality identification, said determined spatial scattering and said determined chromatic impact
further wherein said housing additionally comprises a focusing mechanism in communication with said control circuitry, said control circuitry additionally configured to automatically adjust a position of an objective lens: by means of said adjustment, said image is focusable onto target tissue.

2. The apparatus of claim 1, wherein said control circuitry is further configured to determine the amount of absorption of said output narrow band light within the target area responsive to said signal output by said at least one light sensor responsive to said narrow band light, and
wherein said output tissue information signal is further responsive to said determined absorption amount.

3. The apparatus of claim 1, wherein said at least one light sensor comprises:
an imager configured to output the image of the target area to said control circuitry; and
a light sensor array configured to output the signal responsive to said sensed narrow band light.

4. The apparatus of claim 1, wherein said output narrow band light is coherent.

5. The apparatus of claim 1, wherein in the event that said determined spatial scattering of said sensed narrow band light is indicative of unhealthy tissue within the target area said control circuitry is further configured to determine the amount of absorption of said output narrow band light within the target area responsive to said narrow band light sensed by said at least one light sensor, and
wherein said output tissue information signal is further responsive to said determined absorption amount.

6. The apparatus of claim 5, wherein in the event that said determined absorption amount is not indicative of unhealthy tissue within the target area, said control circuitry is further configured to:
repeat said image abnormality identification; and
repeat said determination of spatial scattering,
wherein said output tissue information signal is further responsive to said repeated image abnormality identification and said repeated determined spatial scattering.

7. The apparatus of claim 5, wherein in the event that said determined absorption amount is indicative of unhealthy tissue within the target area, said output tissue information signal comprises an indication that cervical intraepithelial neoplasia (CIN) is present within tissue of the target area.

8. The apparatus of claim 5, wherein in the event that said image abnormality identification, said determined spatial scattering and said determined chromatic impact are each indicative of unhealthy tissue within the target area, said absorption amount is not determined.

9. The apparatus of claim 8, wherein in the event that said determined chromatic impact and said determined absorption amount are each indicative of unhealthy tissue within the target area said output tissue information signal comprises an indication that grade 3 CIN (CIN3) is present within tissue under the surface of the target area, and
wherein in the event that said determined chromatic impact is not indicative of unhealthy tissue within the target area and said determined absorption amount is indicative of unhealthy tissue within the target area said output tissue information signal comprises an indication that grade 2 CIN (CIN2) is present within tissue of the target area.

10. The apparatus of claim 1, wherein in the event that said image abnormality identification is indicative of unhealthy tissue within the target area and one of said determined chromatic impact and said determined spatial scattering is not indicative of unhealthy tissue within the target area, said output tissue information signal comprises one of:
an indication that cervical polyps are present within tissue of the target area; and
an indication that a benign tumor is present within tissue of the target area.

11. The apparatus of claim 1, wherein in the event that said determined spatial scattering is not indicative of unhealthy tissue within the target area and said determined chromatic impact is indicative of unhealthy tissue within the target area, said control circuitry is further configured to:
repeat said image abnormality identification; and
repeat said determination of spatial scattering,
wherein said output tissue information signal is further responsive to said repeated image abnormality identification and said repeated determined spatial scattering.

12. The apparatus of claim 1, wherein in the event that said image abnormality identification, said determined spatial scattering and said determined chromatic impact are each indicative of unhealthy tissue within the target area, said control circuitry is further configured to determine if the target area image output by said at least one broad band light sensor is indicative of a cancerous tumor within tissue of the target area,
in the event that said control circuitry determines that the target area image is indicative of the cancerous tumor said output tissue information signal comprises an indication that a cancerous tumor is present within tissue of the target area, and
in the event that said control circuitry determines that the target area image is not indicative of the cancerous tumor said output signal comprises an indication that CIN3 is present within tissue of the surface of the target area.

13. The apparatus of claim 1, wherein said control circuitry is further configured to:
determine the correlation between said output image of the target area and an image of group B *streptococcus*; and
output a correlation signal responsive to said correlation determination.

14. The apparatus of claim 1, wherein said intensity abnormality identification is determinable from at least one of: a ratio of a number of pixels with intensity greater than an average intensity to a number of pixels with intensity less than an average intensity and a ratio of high-frequency components of a Fourier transform to lower-frequency components of a Fourier transform.

15. The apparatus of claim 1, wherein said broadband light and said narrow band light provide diagnosis in multiple depths of target tissue.

16. A method of diagnosis of tissue disease, the method comprising:
  receiving an output of at least one light sensor configured to:
    sense broad band light after interaction with a target area of an organ, the broad band light output by a broad band light source configured to irradiate the target area of the organ;
    output an image of the target area responsive to the sensed broad band light;
    sense narrow band light after interaction with the target area, the narrow band light output by a narrow band light source configured to irradiate the target area; and
    output a signal responsive to the sensed narrow band light,
  receiving an output of a color sensor configured to sense the broad band light after interaction with the target area, the broad band light source, narrow band light source, at least one light sensor and color sensor situated within a housing;
  identifying an abnormality in the received target area image responsive to one of the intensity and color of the received target area image;
  determining spatial scattering of the narrow band light sensed by the at least one light sensor;
  determining chromatic impact of the interaction of the broad band light with the target area, responsive to the broad band light sensed by the color sensor; and
  outputting a tissue information signal responsive to said image abnormality identification, determined spatial scattering and determined chromatic impact
  wherein said broadband light and said narrow band light provide diagnosis in multiple depths of target tissue.

17. The method of claim 16, further comprising determining the amount of absorption of the narrow band light within the target area responsive to the narrow band light sensed by the at least one light sensor, wherein said output tissue information signal is further responsive to said determined absorption amount.

18. The method of claim 16, wherein the at least one light sensor comprises:
  an imager configured to output the image of the target area; and
  a light sensor array configured to output the signal responsive to the sensed narrow band light.

19. The method of claim 16, wherein the output narrow band light is a coherent narrow band light.

20. The method of claim 16, wherein in the event that said determined spatial scattering of the sensed narrow band light is indicative of unhealthy tissue within the target area the method further comprises determining the amount of absorption of the narrow band light within the target area responsive to the narrow band light sensed by the at least one light sensor, wherein said output tissue information signal is further responsive to said determined absorption amount.

21. The method of claim 20, wherein in the event that said determined absorption amount is not indicative of unhealthy tissue within the target area the method further comprises:
  repeating said image abnormality identifying;
  repeating said spatial scattering determining,
  wherein said output tissue information signal is further responsive to said repeated image abnormality identification and said repeated determined spatial scattering.

22. The method of claim 20, wherein in the event that said determined absorption amount is indicative of unhealthy tissue within the target area said output tissue information signal comprises an indication that cervical intraepithelial neoplasia (CIN) is present within tissue of the target area.

23. The method of claim 20, wherein in the event that said image abnormality identification, said spatial scattering and said chromatic impact are each indicative of unhealthy tissue within the target area, said absorption amount is not determined.

24. The method of claim 23, wherein in the event that said determined chromatic impact and said determined absorption amount are each indicative of unhealthy tissue within the target area said output tissue information signal comprises an indication that grade 3 CIN (CIN3) is present within tissue under the surface of the target area, and
  wherein in the event that said determined chromatic impact is not indicative of unhealthy tissue within the target area and said determined absorption amount is indicative of unhealthy tissue within the target area said output tissue information signal comprises an indication that grade 2 CIN (CIN2) is present within tissue of the target area.

25. The method of claim 16, wherein in the event that said image abnormality identification is indicative of unhealthy tissue within the target area and one of said determined chromatic impact and said determined spatial scattering is not indicative of unhealthy tissue within the target area, said output tissue information signal comprises one of:
  an indication that cervical polyps are present within tissue of the target area; and
  an indication that a benign tumor is present within tissue of the target area.

26. The method of claim 16, wherein in the event that said determined spatial scattering is not indicative of unhealthy tissue within the target area and said determined chromatic impact is indicative of unhealthy tissue within the target area, the method further comprises:
  repeating said image abnormality identifying; and
  repeating said spatial scattering determining,
  wherein said output tissue information signal is further responsive to said repeated image abnormality identification and said repeated determined spatial scattering.

27. The method of claim 16, wherein in the event that said image abnormality identification, said determined spatial scattering and said determined chromatic impact are each indicative of unhealthy tissue within the target area the method further comprises determining if said received target area image is indicative of a cancerous tumor within tissue of the target area,
  in the event that the target area image is indicative of the cancerous tumor said output tissue information signal comprises an indication that a cancerous tumor is present within tissue of the target area, and
  in the event that the target area image is not indicative of the cancerous tumor said output tissue information said output tissue information signal comprises an indication that CIN3 is present within tissue of the surface of the target area.

28. The method of claim 16, further comprising:
  determining the correlation between said received target area image and an image of group B *streptococcus*; and
  outputting a correlation signal responsive to said correlation determining.

29. The method of claim 16, additionally comprising a step of determining said intensity abnormality identification from at least one of: a ratio of a number of pixels with intensity greater than an average intensity to a number of pixels with intensity less than an average intensity and a ratio of high-frequency components of a Fourier transform to lower-frequency components of a Fourier transform.

30. The apparatus of claim 1, additionally comprising a step of providing diagnosis in multiple depths of target tissue by means of said broadband light and said narrow band light.

* * * * *